US010969395B2

(12) United States Patent
Rogers et al.

(10) Patent No.: US 10,969,395 B2
(45) Date of Patent: Apr. 6, 2021

(54) EPIDERMAL MICROFLUIDIC SENSOR FOR SWEAT COLLECTION AND ANALYSIS FROM AQUATIC ATHLETES

(71) Applicant: NORTHWESTERN UNIVERSITY, Evanston, IL (US)

(72) Inventors: John A. Rogers, Wilmette, IL (US); Jungil Choi, Chicago, IL (US); Johnathan T. Reeder, Plano, TX (US)

(73) Assignee: NORTHWESTERN UNIVERSITY, Evanston, IL (US)

(*) Notice: Subject to any disclaimer, the term of this patent is extended or adjusted under 35 U.S.C. 154(b) by 0 days.

(21) Appl. No.: 16/616,859

(22) PCT Filed: Jun. 1, 2018

(86) PCT No.: PCT/US2018/035691
§ 371 (c)(1),
(2) Date: Nov. 25, 2019

(87) PCT Pub. No.: WO2018/223058
PCT Pub. Date: Dec. 6, 2018

(65) Prior Publication Data
US 2020/0088739 A1 Mar. 19, 2020

Related U.S. Application Data

(60) Provisional application No. 62/514,468, filed on Jun. 2, 2017.

(51) Int. Cl.
*G01N 33/68* (2006.01)
*A61B 5/145* (2006.01)
(Continued)

(52) U.S. Cl.
CPC ..... *G01N 33/6881* (2013.01); *A61B 5/14517* (2013.01); *A61B 5/6833* (2013.01);
(Continued)

(58) Field of Classification Search
CPC .......... G01N 33/6881; G01N 33/54366; A61B 35/14517; A61B 5/6833; A61B 2503/10;
(Continued)

(56) References Cited

U.S. PATENT DOCUMENTS 4,960,467 A 10/1990 Peck
5,464,387 A * 11/1995 Haak ................... A61K 9/0009
604/20

(Continued)

FOREIGN PATENT DOCUMENTS

WO 2009025698 A1 2/2009
WO 2009035773 A1 3/2009
(Continued)

OTHER PUBLICATIONS

United States Patent and Trademark Office (ISR/US) "International Search Report for PCT/US2018/035691", US, Aug. 23, 2018.
(Continued)

*Primary Examiner* — Eric F Winakur
*Assistant Examiner* — Abid A Mustansir
(74) *Attorney, Agent, or Firm* — Locke Lord LLP; Tim Tingkang Xia, Esq.

(57) ABSTRACT

Provided herein are epidermal microfluidic systems and methods that allow for the collection of biofluids in a wet or aquatic environment, for example, from the surface of the skin. The described systems allow for the efficient collection of biofluids, without loss of the biofluid to the surrounding environment or introduction of extraneous liquids from the environment. The described microfluidic systems are versatile and can provide information regarding a number of biofluid properties both electronically and colorimetrically/visually.

54 Claims, 33 Drawing Sheets

(51) Int. Cl.
  *A61B 5/00* (2006.01)
  *C12M 3/06* (2006.01)
  *G01N 33/543* (2006.01)

(52) U.S. Cl.
  CPC ....... *C12M 23/16* (2013.01); *G01N 33/54366* (2013.01); *A61B 2503/10* (2013.01); *A61B 2562/164* (2013.01)

(58) Field of Classification Search
  CPC ..... A61B 2562/164; A61B 5/00; A61B 5/145; C12M 23/16
  See application file for complete search history.

(56) References Cited

U.S. PATENT DOCUMENTS

| | | |
|---|---|---|
| 6,198,953 B1 | 3/2001 | Webster et al. |
| 2003/0109775 A1* | 6/2003 | O'Neil ............... A61B 5/14552 600/323 |
| 2006/0253011 A1 | 11/2006 | Edmonson et al. |
| 2007/0027383 A1 | 2/2007 | Peyser et al. |
| 2007/0179371 A1 | 8/2007 | Peyser et al. |
| 2010/0179403 A1 | 7/2010 | Martinsen et al. |
| 2017/0100102 A1* | 4/2017 | Heikenfeld .......... A61B 5/0531 |
| 2018/0340903 A1* | 11/2018 | Heikenfeld ........... A61B 5/053 |

FOREIGN PATENT DOCUMENTS

| | | |
|---|---|---|
| WO | 2010030609 A1 | 3/2010 |
| WO | 2015168515 A1 | 11/2015 |
| WO | 2016025438 A1 | 2/2016 |
| WO | 2016025468 A2 | 2/2016 |
| WO | 2017004576 A1 | 1/2017 |
| WO | 2017218878 A1 | 12/2017 |
| WO | 2018067412 A1 | 4/2018 |

OTHER PUBLICATIONS

Choi, et al., "Thin, Soft, Skin-Mounted Microfluidic Networks with Capillary Bursting Valves for Chrono-Sampling of Sweat", Adv. Healthcare Mater., 2017.
Koh, et al., "A Soft, Wearable Microfluidic Device for the Capture, Storage, and Colorimetric Sensing of Sweat", Sci. Transl. Med., 2016.
Japanese Patent Office, "First Japanese Office Action for JP Application No. 2019-566268", Japan, Jun. 22, 2020.

* cited by examiner

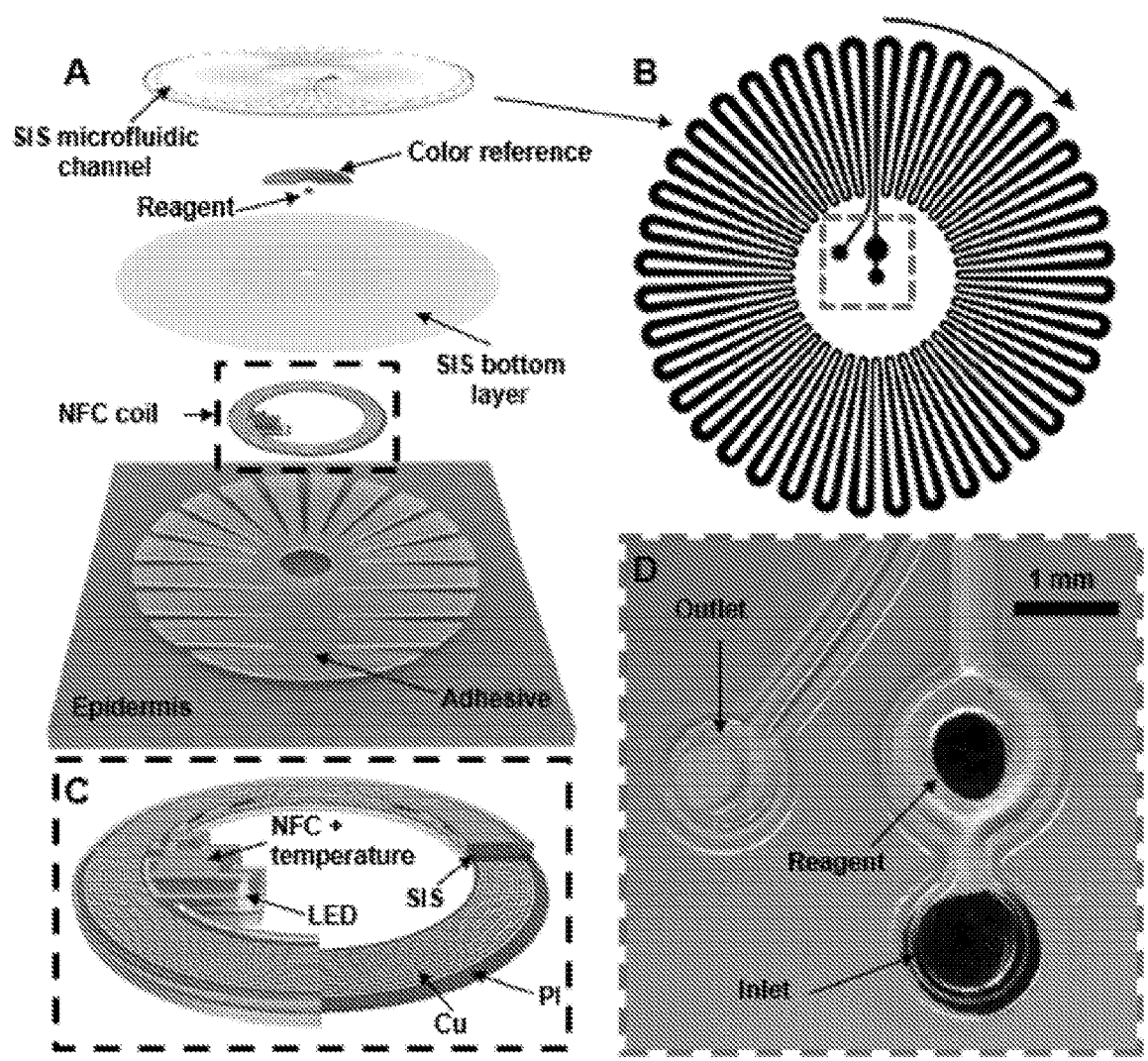
FIG. 4A-D

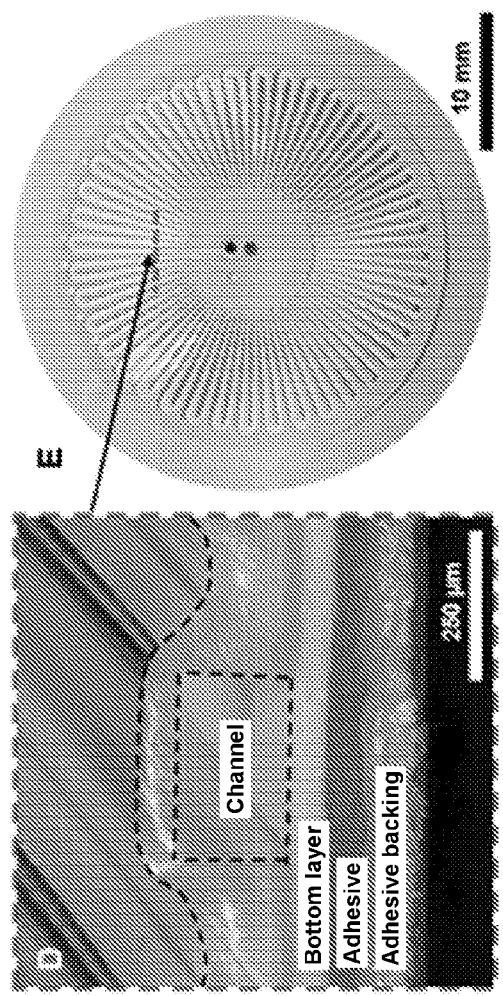
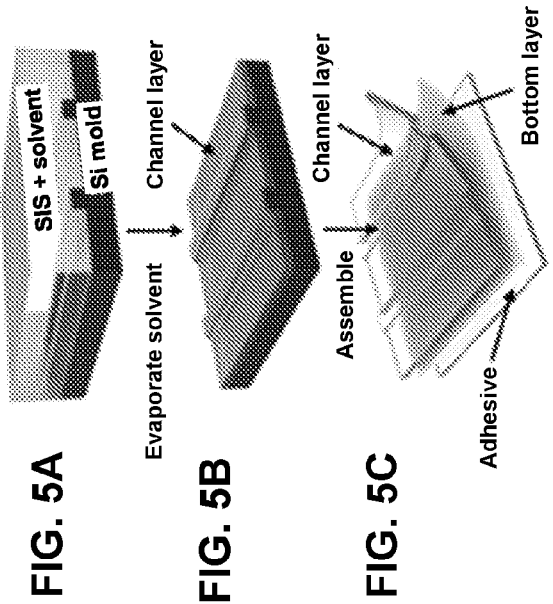
FIG. 5A  FIG. 5B  FIG. 5C  FIG. 5D  FIG. 5E

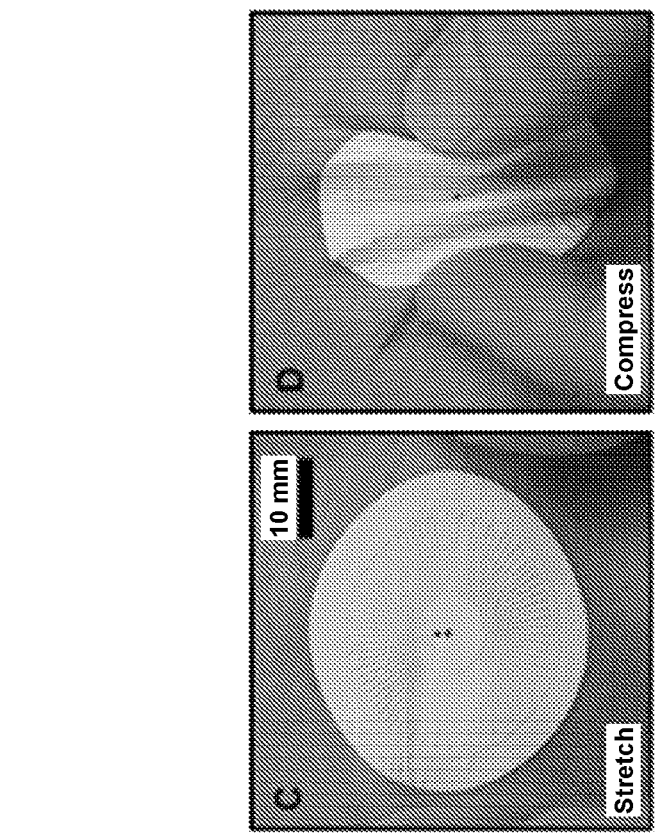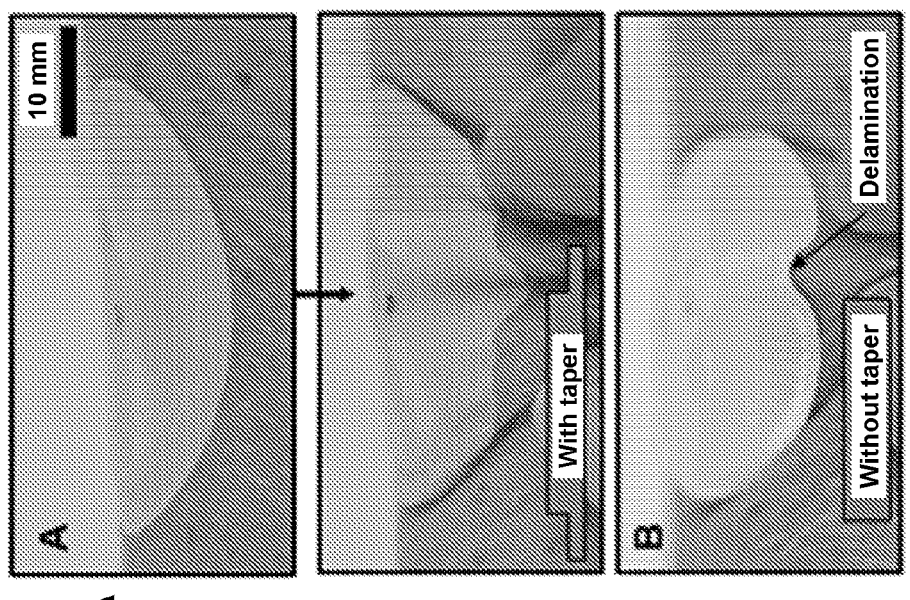
FIG. 6D
FIG. 6C
FIG. 6A
FIG. 6B

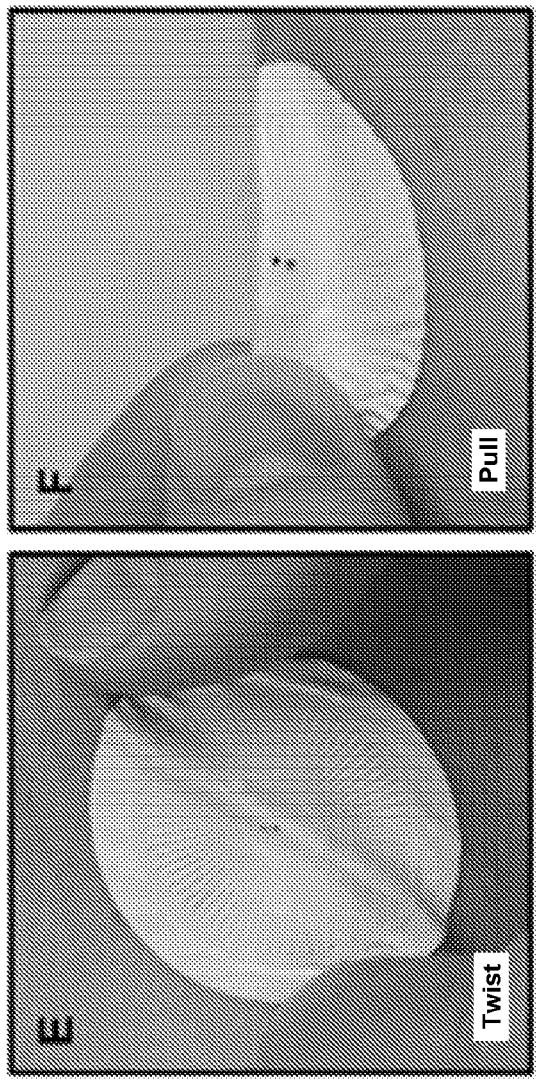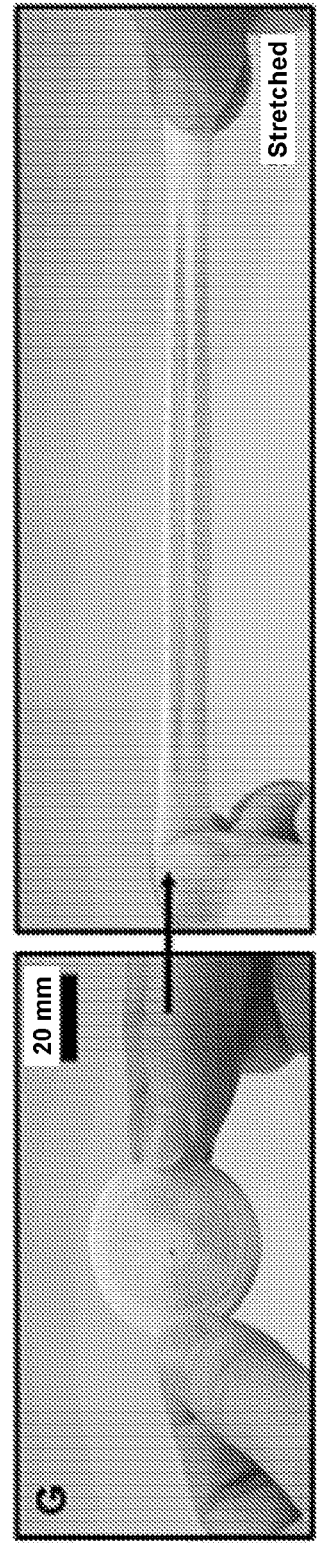
FIG. 6F  FIG. 6E  FIG. 6G

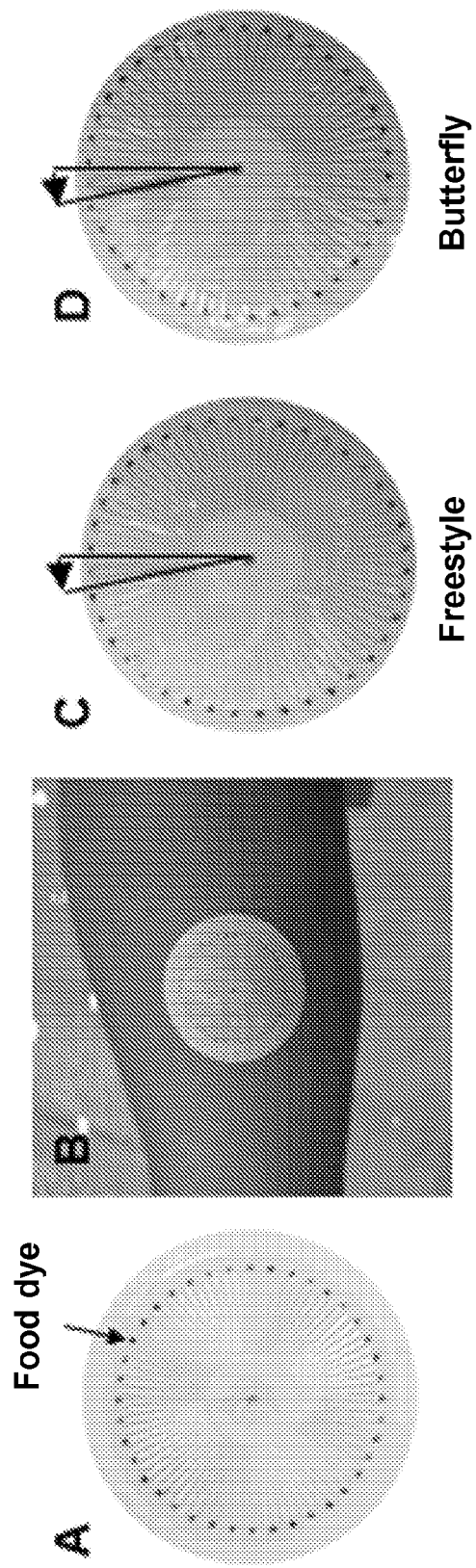

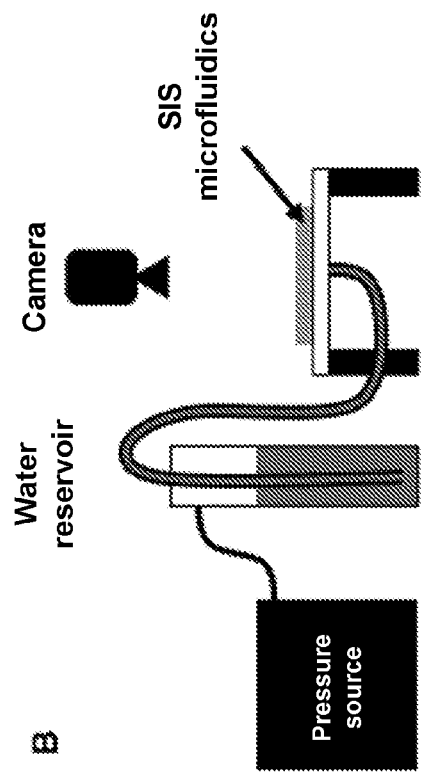
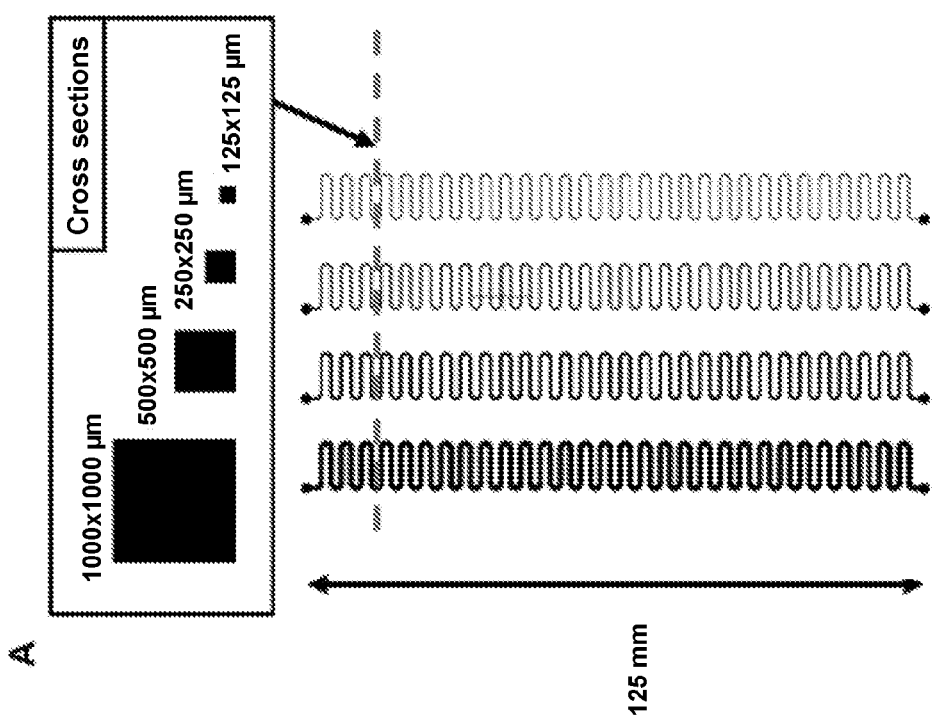
FIG. 9B
FIG. 9A

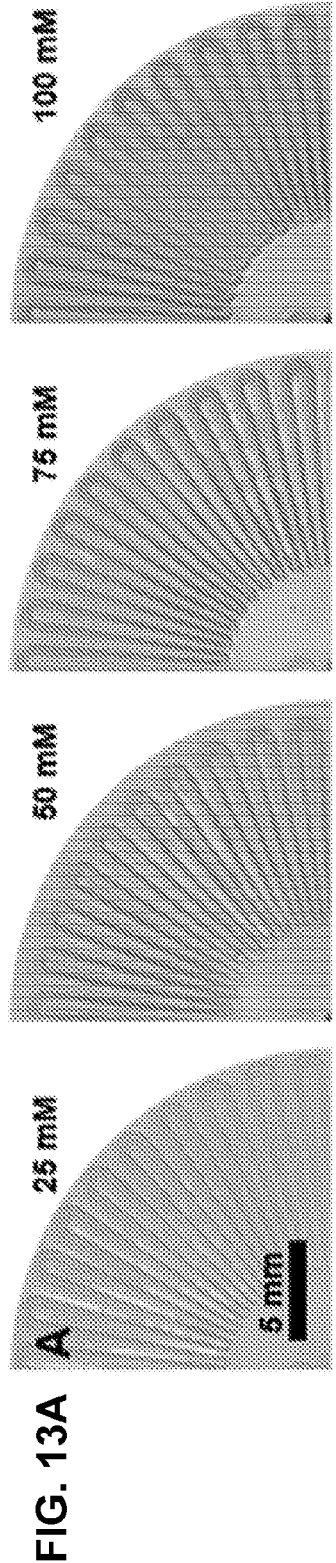
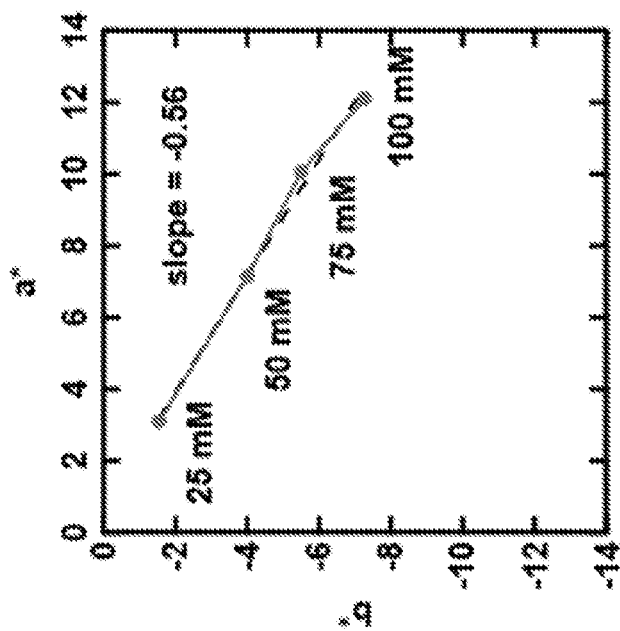
FIG. 13A
FIG. 13B

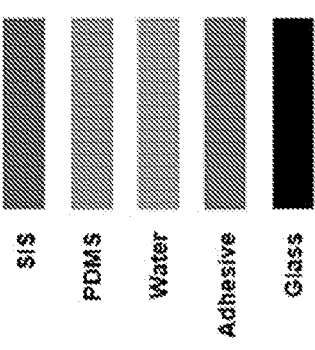
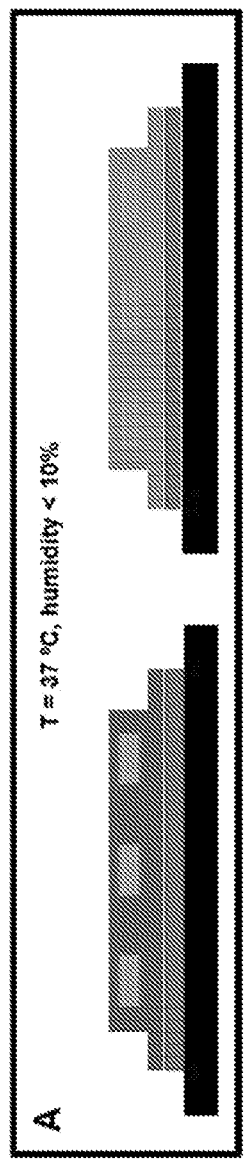
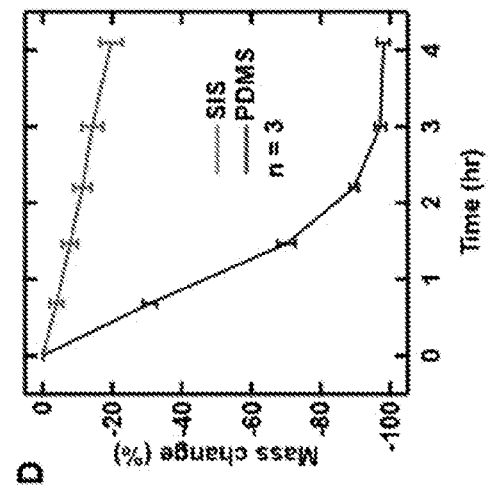
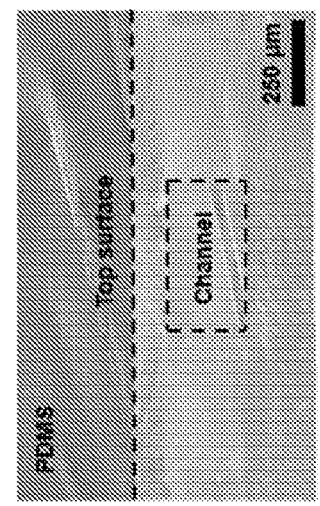
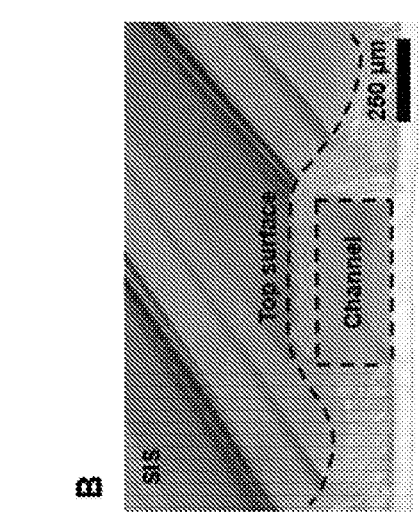
FIG. 20A  FIG. 20B  FIG. 20C  FIG. 20D

EPIDERMAL MICROFLUIDIC SENSOR FOR SWEAT COLLECTION AND ANALYSIS FROM AQUATIC ATHLETES

CROSS-REFERENCE TO RELATED APPLICATIONS

This application claims the benefit of priority to U.S. Provisional Patent Application No. 62/514,468 filed on Jun. 2, 2017, which is specifically incorporated by reference to the extent not inconsistent herewith.

BACKGROUND OF INVENTION

Microfluidics provides a versatile technology platform influencing a wide range of industries and commercial products. In the field of medical diagnostics, for example, microfluidics has been essential to the development of entirely new classes of sensors and assays with potential for revolutionizing medical diagnosis and the treatment of disease. Lab on a chip and microarray systems, for example, have been developed for clinical pathology taking advantage of microfluidic sample collection, preparation and handling to achieve highly sensitivity and rapid point of care analysis of biomarkers in minute quantities of biofluid. The advances in microfluidics have also been leveraged to support other biotechnology and medical applications including high throughput DNA sequencing, mass spectrometry-based proteomics, cellular expression and imaging.

Wearable systems are another technology for which advances in microfluidics has potential to enable new classes of products and advanced modes of functionality. Recent developments in epidermal electronics, for example, provide a class of skin-mounted sensors and actuators compatible with efficient microfluidic sampling at the interface of the skin. Such microfluidics-enabled epidermal systems have potential to support a broad range of clinical applications in healthcare including analysis of biomarkers, drug administration, and real time diagnosis and monitoring of medical conditions including diabetes, inflammation and hydration state. [see, e.g., US20060253011; U520100179403; WO 2016/025468; WO 2016/025438; WO2010030609; US20070027383; US20070179371A1; U.S. Pat. Nos. 4,960, 467; 6,198,953; and WO2009025698A1].

As will be understood from the forgoing, the development of wearable systems is needed having physical formats and mechanical properties providing a robust interface with the skin to achieve quantitatively reliable collection and handling of biofluids over clinically relevant time intervals, specifically in wet or aquatic environments. In addition, microfluidic systems are needed that are capable of effective collection, pretreatment, storage and analysis of biofluids to support a range of applications for wearable systems including medical diagnostics and therapy.

SUMMARY OF THE INVENTION

Provided herein are microfluidic systems and methods that allow for the collection of biofluids in a wet or aquatic environment, for example, from the surface of the skin. The described systems allow for the efficient collection of biofluids, without loss of the biofluid to the surrounding environment or introduction of extraneous liquids from the environment. The described microfluidic systems are versatile and can provide information regarding a number of biofluid properties both electronically and colorimetrically/visually.

In an aspect, provided is an epidermal microfluidic system for use in a wet environment, the system comprising: i) a flexible substrate; ii) a microfluidic inlet conduit network at least partially embedded in or supported by the flexible substrate; iii) a biofluid inlet fluidically connected to the microfluidic inlet conduit network to provide a biofluid from a skin surface to the microfluidic inlet conduit during use; iv) a microfluidic outlet conduit network fluidically connected to the microfluidic inlet conduit network and configured to relieve gas back pressure from the microfluidic inlet conduit network and sized to maintain liquid integrity of the system from the wet environment during use; and v) at least one colorimetric sensor.

In an aspect, provided is an epidermal microfluidic system for use in a wet environment, the system comprising: i) a flexible substrate; ii) a microfluidic inlet conduit network at least partially embedded in or supported by the flexible substrate; iii) a biofluid inlet fluidically connected to the microfluidic inlet conduit network to provide a biofluid from a skin surface to the microfluidic inlet conduit during use; iv) a plurality of reservoir chambers, each reservoir chamber fluidically connected with the microfluidic inlet conduit network; v) a microfluidic outlet conduit network fluidically connected to the plurality of reservoir chambers and configured to relieve gas back pressure from the microfluidic inlet conduit network and sized to maintain liquid integrity of the system from the wet environment during use; and vi) at least one colorimetric sensor.

The devices described herein may comprise multiple stacked layers to add additional functionalities or protect components and reduce the risk of extraneous environmental fluids entering the system. The devices may have a tapered geometry that increases the adhesion to the skin, promotes the formation of a seal to prevent extraneous liquid from reaching the inlet and reduces the risk of delamination. The described devices may be flexible, stretchable and may establish conformal contact with the underlying skin surface.

The system may further comprise a capping layer covering a skin-facing or outer-facing surface of the flexible substrate. The flexible substrate and the capping layer may independently comprise a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, poly (styrene-isoprene-styrene), chitosan, and any combination thereof.

The capping layer may comprise a first auxiliary inlet aligned with the biofluid inlet in a direction that is perpendicular to a plane formed by the flexible substrate skin-facing surface. The flexible substrate has a first diameter and the capping layer may have a second diameter different from the first diameter of the flexible substrate, for example less than or equal to 80%, 90% or 95% of the first diameter of the flexible substrate.

The system may further comprise an adhesive layer positioned on at least a portion of an exposed surface of the capping layer; wherein the adhesive layer comprises a second auxiliary inlet fluidically aligned with the biofluid inlet. The adhesive layer may be capable of reversibly adhering the system to the skin surface. The adhesive layer may comprise medical grade acrylic.

The flexible substrate may have an average thickness selected from the range of 100 µm to 5 mm, 500 µm to 2 mm, or optionally less than or equal to 500 µm. The capping layer may have an average thickness selected from the range of 50 µm to 1 mm, 100 µm to 500 µm, or optionally, less than or equal to 500 µm. The adhesive layer may have an average thickness selected from the range of 50 µm to 500 µm, 10 µm to 100 µm, or optionally, less than or equal to 50 µm.

The described devices may utilize colorimetric sensing to provide visual feedback regarding the biofluid to a wearer, trainer or health care professional. The colorimetric sensors may quantify the volume of the biofluid being collected to the device, which then may be extrapolated or correlated to the total biofluid being produced by the wearer. Additionally, colorimetric sensors may provide information regarding the composition of the biofluid.

The colorimetric sensor may be a dye in fluidic communication with the microfluidic inlet network. At least a portion of the dye may be mixed with the biofluid when the biofluid enters the microfluidic inlet network, thereby providing a visual indication of fluid flow (indicating volume and flow rate) through the microfluidic inlet network.

The system may further comprise a plurality of colorimetric sensors positioned in fluidic communication with the microfluidic inlet network. Each colorimetric sensor may be positioned in a unique reservoir chamber to measure a biofluid property. Each colorimetric sensor may comprise a dye to indicate the presence of the biofluid in the reservoir or the microfluidic inlet network.

The colorimetric sensors may comprise one or more color-responsive reagents for quantification of a biofluid volume or amount, flow rate, composition or any combination of thereof, for example, color-responsive reagents that are indicator reagents that react with liquid water or react with one or more analytes in the biofluid. The color-responsive reagents may comprise a silver chloranilate suspension. The color-responsive reagents may be insensitive to humidity, for example, usable at 100% humidity without interacting with vapor in the environment.

The color-responsive reagents may be immobilized in a respective reservoir of the plurality of chamber reservoirs. For example, the color-responsive reagents may be selected from the group consisting of dye, $CoCl_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator, silver chloranilate and any combination thereof.

The described systems prevent extraneous fluids from entering the device or mixing with the collected biofluid even during strenuous exercise, such as swimming or diving.

The microfluidic outlet conduit network comprises may comprise a biofluid outlet having a characteristic dimension selected to prevent liquid backfilling from the surrounding wet environment, for example, a cross-sectional area less than or equal to 1 $mm^2$, 0.6 $mm^2$, or optionally, 0.4 $mm^2$.

The biofluid inlet may have a characteristic dimension configured to facilitate biofluid entry to the microfluidic network, for example, a cross-sectional area greater than or equal to 0.5 $mm^2$, 1 $mm^2$, or optionally, 3 $mm^2$. For example, each of one or more cross-sectional areas of the microfluidic outlet conduit network may be selected from the range of 0.1 $mm^2$ to 0.3 $mm^2$.

The microfluidic inlet conduit network may collect at least a portion of biofluid released from a skin surface via capillary action, a pressure differential or a combination of thereof. The microfluidic inlet conduit network may further comprise one or more passive valves or one or more active valves configured to allow for time dependent collection, analysis or storage of biofluid. The passive or active valves may be direction-selective valves. The passive or active valves may be selective super absorbent polymer (SAP) valves, hydrophobic valves or a combination thereof, the passive or active valves may be configured to close after a reservoir or channel is filled with biofluid, thereby preventing loss or release of collected biofluid from a filled reservoir or channel.

The biofluid may be sweat. The gas may be air. The color-responsive reagent may be unresponsive with exposure to 100% relative humidity for a time period of at least 24 hours. The microfluidic outlet conduit network may maintain the liquid integrity of the system with the surrounding environment by preventing introduction of liquid into the reservoir chambers. The flexible substrate may be capable of conformal contact with a skin surface.

The microfluidic inlet conduit network may have a circular serpentine geometry, for example, a serpentine geometry having a number of turns or loops greater than or equal to 10, 25, or optionally, 40. Each of the turn or loop may have a volume less than or equal to 10 µm, 5 µm, or optionally 3 µm. The microfluidic inlet conduit network may have a depth of less than or equal to 500 µm and a width selected from the range of 100 µm to 800 µm. The flexible substrate and/or the capping layer may be poly(styrene-isoprene-styrene).

The plurality of reservoir chambers may be evenly distributed along a length of the microfluidic inlet conduit network in a serial configuration. The microfluidic inlet conduit network may comprise a common inlet conduit that with a plurality of inlet chamber conduits that fluidically connect each of the reservoir chambers to the common inlet conduit at a single connection. The microfluidic outlet conduit network may comprise a circumferential common outlet conduit having a plurality of chamber conduits that fluidically connect each of the reservoir chambers to the circumferential common outlet at a plurality of outlet connections. The plurality of chamber conduits may be greater than or equal to 2 and less than or equal to 4. Each of the plurality of chamber conduits may connect to a chamber reservoir at a chamber constriction connection.

The common inlet conduit may be positioned in an interior region of the flexible substrate and the circumferential common outlet conduit is positioned in an exterior region of the flexible substrate, with the plurality of reservoir chambers extending between the common inlet conduit and the circumferential outlet conduit.

The system has a total microfluidic volume and the plurality of reservoir chambers may represent at least 50% of the total microfluidic volume.

The system may further comprise a temperature sensor. The temperature sensor may be embedded in or supported by the flexible substrate and may provide a body temperature of a wearer of the system.

The system may further comprise a wireless device. The wireless device may be a transmitter, a receiver or both. The wireless device may be a near-field communication (NFC) coil. The wireless device may be wirelessly powered.

The system may further comprise at least one light emitting diode (LED). The LED may provide feedback to a wearer of the system regarding the biofluid.

In an aspect, provided is an epidermal microfluidic system for use in a wet environment, the system comprising: i) a flexible substrate; ii) a capping layer supported by the flexible substrate;
  wherein the capping layer has a diameter less than that of the flexible substrate, thereby forming a tapered geometry;
  iii) a microfluidic inlet conduit network having a circular serpentine geometry at least partially embedded in or supported by the flexible substrate, the capping layer or both the flexible substrate and the capping layer; iv) a biofluid inlet fluidically connected to the microfluidic inlet conduit network to provide a biofluid from a skin surface to the microfluidic inlet conduit during use; v) a microfluidic outlet conduit network fluidically connected to the microfluidic inlet conduit network and configured to relieve gas back pressure from the microfluidic inlet conduit network and sized to maintain liquid integrity of the system from the wet environment during use; vi) a dye in fluidic communication with the microfluidic inlet conduit network, wherein the dye mixes with the biofluid upon entry of the microfluidic inlet conduit network, thereby providing a visual indicator of the flow of the biofluid through the microfluidic inlet conduit network.

The system may further comprise a temperature sensor embedded in or supported by the flexible substrate, wherein the temperature sensor provides a body temperature of a wearer of the system. The system may further comprise a NFC coil embedded in or supported by the flexible substrate.

In an aspect, provided is a method for measuring a biofluid property comprising: i) mounting an epidermal microfluidic system of any of the above claims to a skin surface; ii) collecting the biofluid from the skin surface via capillary action, a pressure differential or a combination of these; iii) introducing the biofluid to at least one of the colorimetric sensors via the microfluidic inlet conduit network; and iv) measuring a biofluid property using the at least one colorimetric sensor.

In an aspect, provided is a method for measuring a biofluid property comprising: i) providing an epidermal microfluidic system comprising: a) a flexible substrate; b) a microfluidic inlet conduit network at least partially embedded in or supported by the flexible substrate; c) a biofluid inlet fluidically connected to the microfluidic inlet conduit network to provide a biofluid from a skin surface to the microfluidic inlet conduit during use; d) a microfluidic outlet conduit network fluidically connected to the microfluidic inlet conduit network and configured to relieve gas back pressure from the microfluidic inlet conduit network and sized to maintain liquid integrity of the system from the wet environment during use; and e) at least one colorimetric sensor; ii) mounting the epidermal microfluidic system on to a skin surface of a wearer; iii) collecting the biofluid from the skin surface via capillary action, a pressure differential or a combination of these; iv) determining a property of the biofluid via the at least one colorimetric sensor. One skilled in the art will recognize that the various systems and components described herein may also be used in the methods, as described herein.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

BRIEF DESCRIPTION OF THE DRAWINGS

FIG. 4 provides a waterproof epidermal microfluidic and electronic patch. FIG. 4A is an exploded view of the device layers. FIG. 4B provides an example of a circular serpentine geometry.

FIG. 4C provides the near field communication coil (NFC) for wireless skin temperature sensing. FIG. 4D is a micrograph showing the microfluidic inlet and outlet and colorimetric reagent.

FIG. 5 provides example fabrication and characterization of SIS microfluidic systems. FIG. 5A SIS is cast on a bas-relief wafer. FIG. 5B evaporation of the solvent leaves behind a thing, conformal SIS coating on the wafer. FIG. 5C the channel layer, bottom layer and adhesive are laminated together and bonded via light pressing after demolding. FIG. 5D provides an epifluidic device after fabrication and assembly. FIG. 5E is a cross-sectional micrograph of the microfluidic channel showing the contoured geometry of the top surface.

FIG. 7 illustrates environmental backfilling due to hydrostatic pressure and impact. FIG. 7A shows a device used for backfilling tests. Food dye deposited at the top of teach turn in the microfluidic channel indicates the extent to which environmental water has proceeded up the channel. FIG. 7B the device after attaching to the forearm. FIG. 7C the backfilling in the device after swimming 100 m of freestyle (crawl stroke). FIG. 7D the backfilling of the device after swimming 100 m of butterfly.

FIG. 9 provides the setup for measuring flow rate through SIS-based microfluidic devices. FIG. 9A provides the channel geometry for microfluidic flow rate test samples. FIG. 9B provides an experimental setup for measuring fluid flow rate.

FIG. 11 illustrates the mechanical effect of the tapered edge and SIS thickness.

FIG. 12 illustrates the impact of adhesive geometry on sweat collection.

FIG. 13 illustrates color calibration for chloride sensing. FIG. 13A provides images of SIS devices with silver chloranilate reagent after with the reference concentrations FIG. 13B provides the a* and b* color values of reference chloride concentrations after reacting with silver chloranilate.

FIG. 15 provides the waterproof NFC components.

FIG. 16 shows sweat collection from aquatic and dryland athletes.

FIG. 17 shows trails with Ironman® athletes.

FIG. 20 provides a comparison of evaporation rate of sweat after collection. FIG. 20A Experimental setup for measuring evaporative water loss from epifluidic devices. FIG. 20B Cross-sectional micrograph of a SIS device. FIG. 20C Cross-sectional micrograph of a PDMS device. FIG. 20D The mass change of PDMS and SIS epifluidic devices after filling with water and heating at 37° C. SIS devices store sweat for 4 hours with less than 20% loss, while PDMS lose approximately 100% within 3 hours.

DETAILED DESCRIPTION OF THE INVENTION

Figure 1:
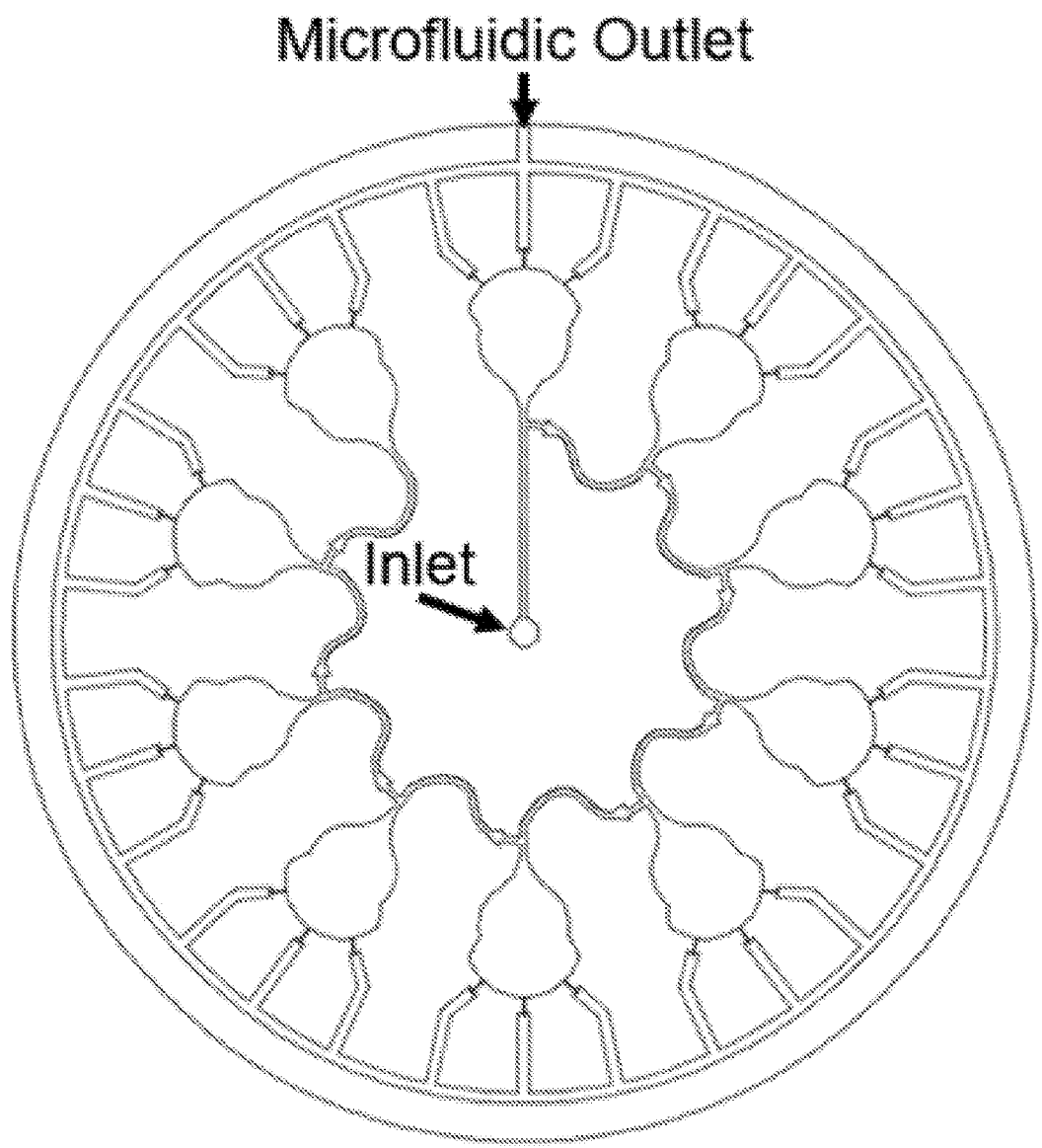
FIG. 1 Illustrates a microfluidic system having an inlet for introducing biofluid (e.g., sweat) to a microfluidic inlet conduit network.

In general, the terms and phrases used herein have their art-recognized meaning, which can be found by reference to standard texts, journal references and contexts known to those skilled in the art. The following definitions are provided to clarify their specific use in the context of the invention.

"Microfluidic device" refers to a system, device or device component containing liquid constrained in at least one physical dimension generally of the order of nanometers to millimeters, optionally nanometers to microns. Microfluidic devices may include structures for collecting, extracting, transporting, storing, analyzing and/or outputting fluids, including biofluids. In some embodiments, the liquid is constrained to a lateral dimension selected over the range of 1 nm and 1 cm, such as a lateral dimension (e.g., depth) selected over the range of 1 nm to 5 mm, 100 nm to 1000 μm or 500 nm to 100 μm, and a lateral dimension (e.g., width) selected over the range of 1 nm to 1 cm, 10 μm to 2 mm or 1 μm to 10 mm. In embodiments, an axial (e.g., flow) direction in a microfluidic system, device or device component can be long, for example on the order of meters, but will more commonly be 0.1 cm to 100 cm or 1 cm to 50 cm. Microfluidics are distinguished herein from macrofluidics. In some embodiments, the invention provides tissue-mounted, optionally skin-mounted, microfluidic devices. Microfluidic devices of some embodiments are capable of determining the composition of a biofluid such as sweat, for example, the presence, absence, and/or amount of one or more biomarkers, optionally as a function of time. Microfluidic devices of some embodiments are capable of determining one or more physical parameters characteristics of a biofluid, such as amount, volume, release rate and/or absorption rate, optionally as a function of time.

"Tissue-mounted" refers to systems, devices or device components having at least one surface capable of being supported, directly or indirectly, by a tissue surface, for example in a configuration providing fluidic communication and/or conformal contact. Epidermal systems and devices are a subset of tissue-mounted systems wherein the system, device or device component has at least one surface capable of being supported, directly or indirectly, by a surface of the skin, for example in a configuration providing fluidic communication and/or conformal contact. The invention provides tissue-mounted devices, such as epidermal systems, capable of collection, storage, treatment, processing, handling and/or analysis of biofluids such as sweat.

The expression "at least partially embedded in" refers to a configuration wherein an element, such as a microfluidic network or component thereof, is at least partially, and optionally wholly, integrated on or within a layer and/or device component, such as a substrate. In an embodiment, for example, "at least partially embedded in" refers to a configuration wherein an embedded element, such as a microfluidic element such as an inlet, outlet, passage, channel, and/or reservoir, at least partially comprises one or more surfaces, recessed features, relief features or any combination thereof, within or on a layer or device component it is at least partially embedded in. In an embodiment, for example, "at least partially embedded in" refers to a configuration wherein an embedded element, such as an inlet, outlet, passage, channel, and/or reservoir, at least partially comprises features molded or embossed on or into a layer or device component it is at least partially embedded in. In an embodiment, for example, "at least partially embedded in" refers to a configuration wherein an embedded element, such as an inlet, outlet, passage, channel, and/or reservoir, at least partially comprises features at least partially comprising surfaces (e.g., top, bottom, walls, etc.) of a layer or device component it is at least partially embedded. In an embodiment, for example, "at least partially embedded in" refers to a configuration wherein an embedded element, such as an inlet, outlet, passage, channel, and/or reservoir, is at least partially covered or encapsulated by another device component, such as a top layer or barrier layer.

"Substrate" refers to a device component, such as a layer, having a surface that is capable of supporting, accommodating, embedding or otherwise integrating a structure, including a microfluidic structure, optical structure, electronic structure, thermal structure or any combination of these. Substrates in some embodiments are capable of supporting, accommodating, embedding or otherwise integrating a device component such as microfluidic device component, optical device component, electronic device component, structural device component or any combination of these. In some embodiments, a substrate is capable of at least partially forming an interface with the tissue of a subject, such as with the epidermis or other organ of a subject. In an embodiment, a substrate of the present devices, systems and methods is a biocompatible and/or bioinert material. In an embodiment, a substrate of the present devices, systems and methods is a polymer or elastomer material. Substrates of the invention include "flexible substrates" which refers to a substrate component for a device having at least one function or purpose in addition to providing mechanical support for a component(s) disposed on or within the substrate such as a microfluidic functionality, a mechanical functionality, optical functionality or a thermal functionality. A flexible substrate may facilitate mechanical, thermal, chemical and/or electrical matching of the flexible substrate and the skin of a subject such that the mechanical, thermal, chemical and/or electrical properties of the flexible substrate and the skin are within 20%, or 15%, or 10%, or 5% of one another. Devices and systems of the invention may have more than one substrate, for example, such as embodiments having a bottom substrate capable of establishing an interface with skin and an upper substrate layer, such as a barrier layer providing an interface with an ambient environment. For example, the invention includes devices and systems having a multilayer geometry including a substrate and barrier layer.

In some embodiments, a substrate is mechanically matched to a tissue, such as mechanically matched to skin. In an embodiment, a mechanically matched substrate is optionally capable of providing an interface for establishing fluid communication and/or conformal contact with a surface of the tissue, such as skin. Devices and methods of certain embodiments incorporate substrates comprising soft materials, for example exhibiting flexibility and/or stretchability, such as polymeric and/or elastomeric materials. In an embodiment, a mechanically matched substrate has a modulus less than or equal to 100 MPa, and optionally for some embodiments less than or equal to 10 MPa, and optionally for some embodiments, less than or equal to 1 MPa. In an embodiment, a mechanically matched substrate has a thickness less than or equal to 0.5 mm, and optionally for some embodiments, less than or equal to 1 cm, and optionally for some embodiments, less than or equal to 3 mm. In an embodiment, a mechanically matched substrate has a bending stiffness less than or equal to 1 nN m, optionally less than or equal to 0.5 nN m.

"Polymer" refers to a macromolecule composed of repeating structural units connected by covalent chemical bonds or the polymerization product of one or more monomers, often characterized by a high molecular weight. The term polymer includes homopolymers, or polymers consisting essentially of a single repeating monomer subunit. The term polymer also includes copolymers, or polymers consisting essentially of two or more monomer subunits, such as random, block, alternating, segmented, grafted, tapered and other copolymers. Useful polymers include organic polymers or inorganic polymers that may be in amorphous, semi-amorphous, crystalline or partially crystalline states. Crosslinked polymers having linked monomer chains are particularly useful for some applications. Polymers useable in the methods, devices and components disclosed include, but are not limited to, plastics, elastomers, thermoplastic elastomers, elastoplastics, thermoplastics and acrylates. Exemplary polymers include, but are not limited to, acetal polymers, biodegradable polymers, cellulosic polymers, fluoropolymers, nylons, polyacrylonitrile polymers, polyamide-imide polymers, polyimides, polyarylates, polybenzimidazole, polybutylene, polycarbonate, polyesters, polyetherimide, polyethylene, polyethylene copolymers and modified polyethylenes, polyketones, poly(methyl methacrylate), polymethylpentene, polyphenylene oxides and polyphenylene sulfides, polyphthalamide, polypropylene, polyurethanes, styrenic resins, sulfone-based resins, vinyl-based resins, rubber (including natural rubber, styrene-butadiene, polybutadiene, neoprene, ethylene-propylene, butyl, nitrile, silicones), acrylic, nylon, polycarbonate, polyester, polyethylene, polypropylene, polystyrene, polyvinyl chloride, polyolefin or any combinations of these.

"Elastomer" refers to a polymeric material which can be stretched or deformed and returned to its original shape without substantial permanent deformation. Elastomers commonly undergo substantially elastic deformations. Useful elastomers include those comprising polymers, copolymers, composite materials or mixtures of polymers and copolymers. Elastomeric layer refers to a layer comprising at least one elastomer. Elastomeric layers may also include dopants and other non-elastomeric materials. Useful elastomers include, but are not limited to, thermoplastic elastomers, styrenic materials, olefinic materials, polyolefin, polyurethane thermoplastic elastomers, polyamides, synthetic rubbers, PDMS, polybutadiene, polyisobutylene, poly(styrene-butadiene-styrene), polyurethanes, polychloroprene and silicones. Exemplary elastomers include, but are not limited to silicon containing polymers such as polysiloxanes including poly(dimethyl siloxane) (i.e., PDMS and h-PDMS), poly(methyl siloxane), partially alkylated poly (methyl siloxane), poly(alkyl methyl siloxane) and poly (phenyl methyl siloxane), silicon modified elastomers, thermoplastic elastomers, styrenic materials, olefinic materials, polyolefin, polyurethane thermoplastic elastomers, polyamides, synthetic rubbers, polyisobutylene, poly(styrene-butadiene-styrene), polyurethanes, polychloroprene and silicones. In an embodiment, a polymer is an elastomer.

"Conformable" refers to a device, material or substrate which has a bending stiffness that is sufficiently low to allow the device, material or substrate to adopt a desired contour profile, for example a contour profile allowing for conformal contact with a surface characterized by a surface topography comprising recessed and/or relief features. In certain embodiments, a desired contour profile is that of tissue, such as skin.

"Conformal contact" refers to contact established between a device and a receiving surface. In one aspect, conformal contact involves a macroscopic adaptation of one or more surfaces (e.g., contact surfaces) of a device to the overall shape of a surface. In another aspect, conformal contact involves a microscopic adaptation of one or more surfaces (e.g., contact surfaces) of a device to a surface resulting in an intimate contact substantially free of voids. In an embodiment, conformal contact involves adaptation of a contact surface(s) of the device to a receiving surface(s) such that intimate contact is achieved, for example, wherein less than 20% of the surface area of a contact surface of the device does not physically contact the receiving surface, or optionally less than 10% of a contact surface of the device does not physically contact the receiving surface, or optionally less than 5% of a contact surface of the device does not physically contact the receiving surface. In some embodiments, devices of the invention are capable of establishing conformal contact with tissue of a subject, such as a portion of the skin of a subject.

"Sensing" refers to an action of detecting the presence, absence, amount, magnitude and/or intensity of one or more physical and/or chemical properties or characteristics. Sensor refers to a device or component thereof that is capable of sensing. Useful device components for sensing include, but are not limited to electrode elements, chemical or biological sensor elements, pH sensors, colorimetric sensors, electrochemical sensors, temperature sensors, strain sensors, mechanical sensors, position sensors, optical sensors and capacitive sensors.

"Actuating" refers to an action of acting on, stimulating, controlling, or otherwise affecting a structure, material or device component. Actuator refers to a device or component thereof that is capable of actuating. Useful device components for actuating include, but are not limited to, electrode elements, electromagnetic radiation emitting elements, light emitting diodes, lasers, magnetic elements, acoustic elements, piezoelectric elements, chemical elements, biological elements, and heating elements.

The terms "flexible" and "bendable" are used synonymously in the present description and refer to the ability of a material, structure, device or device component to be deformed into a curved or bent shape without undergoing a transformation that introduces significant strain, such as strain characterizing the failure point of a material, structure, device or device component. In an exemplary embodiment, a flexible material, structure, device or device component may be deformed into a curved shape without introducing strain larger than or equal to 5%, for some applications larger than or equal to 1%, and for yet other applications larger than or equal to 0.5% in strain-sensitive regions. A used herein, some, but not necessarily all, flexible structures are also stretchable. A variety of properties provide flexible structures (e.g., device components) of the invention, including materials properties such as a low modulus, bending stiffness and flexural rigidity; physical dimensions such as small average thickness (e.g., less than 10000 microns, optionally less than 1000 microns and optionally less than 100 micron) and device geometries such as thin film and mesh geometries.

"Stretchable" refers to the ability of a material, structure, device or device component to be strained without undergoing fracture. In an exemplary embodiment, a stretchable material, structure, device or device component may undergo strain larger than 0.5% without fracturing, for some applications strain larger than 1% without fracturing and for yet other applications strain larger than 3% without fracturing. A used herein, stretchable structures may also be flexible. Some stretchable structures (e.g., device components) are engineered to be able to undergo compression, elongation and/or twisting so as to be able to deform (and optionally operate) without fracturing. Stretchable structures include structures comprising stretchable materials, such as elastomers; and bent, coiled or serpentine structures capable of elongation, compression and/or twisting motion.

Devices of the present invention may optionally include one or more barrier layers. As used herein "barrier layer" refers to a device component spatially separating two or more other device components or spatially separating a device component from a structure, material, fluid or ambient environment external to the device. In one embodiment, a barrier layer encapsulates one or more device components. In embodiments, a barrier layer separates one or more device components from an aqueous solution, a biological tissue and/or a biological environment. In some embodiments, a barrier layer is a passive device component. In some embodiments, a barrier layer is a functional, but non-active, device component. In a specific embodiment, a barrier layer is a moisture barrier. As used herein, the term "moisture barrier" refers to a barrier layer which provides protection to other device components from bodily fluids, ionic solutions, water or other solvents. In one embodiment, a moisture barrier provides protection to an external structure, material or fluid, for example, by preventing leakage current from escaping an encapsulated device component and reaching the external structure, material or fluid.

"Biofluid" refers to fluid generated by, extracted from or otherwise derived from the tissue of a subject, such as an organ of a subject. Biofluids include sweat, tears, saliva, gingival crevicular fluid, interstitial fluid, blood and combinations thereof.

As used herein, the term "fluidically connected" refers to the configuration of two or more components such that a fluid (e.g., a gas or a liquid) is capable of transport, flowing and/or diffusing from one component to another component, without adversely impacting the functionality of each of the components. Components may be in fluid communication via one or more elements such as channels, valves, tubes, containment structures, reservoirs, pumps or any combinations of these. In some embodiments, components in fluid communication are in direct fluid communication wherein fluid is capable of transport directly from one component to another. In some embodiments, components in fluid communication are in indirect fluid communication wherein fluid is capable of transport indirectly from one component to another via one or more intermediate structures separating the components.

The terms "electrical contact" and "electronic contact" refers to the ability of two or more materials and/or structures that are capable of transferring charge between them, such as in the form of the transfer of electrons or ions. The terms "electrical contact" and "electronic contact" may refer to a configuration of two or more components such that an electronic signal or charge carrier can be directly or indirectly transferred from one component to another. As used herein, the terms "electrical contact" and "electronic contact" include one way and two way electrical communication. In some embodiments, components in electrical contact or electronic contact are in indirect electrical communication wherein an electronic signal or charge carrier is indirectly transferred from one component to another via one or more intermediate structures, such as circuit elements, separating the components.

As used herein, the term "electrical load" may refer to voltage or current applied to electrodes, sensors or other device components. The term "electrical response" or "electrical parameter" may refer to a voltage, current, or impedance response of the electrodes or sensors to the electrical load. For example, applying a current between two electrodes (electrical load) may induce a voltage drop between the two electrodes (electrical response). The electrical load may be a DC or an AC load.

The term "BLE" refers to a Bluetooth low energy system.

The term "functionalized" may refer to modification of a material or layer surface to add chemical, physical, electrical, optical or electrochemical functionality. In an embodiment, biological molecules or reagents may be deposited onto an electrode in a process of forming an electrochemical sensor.

The term "wet environment" may refer to the system being in a high-humidity environment or being at least partially surrounded by a liquid. The term "high-humidity" refers to the relative humidity of the surroundings being >70%.

EXAMPLE 1: EPIDERMAL MICROFLUIDIC SENSOR FOR SWEAT COLLECTION AND ANALYSIS FROM AQUATIC ATHLETES

Sweat capture and analysis from aquatic athletes, or athletes in high-humidity environments, presents unique challenges not present in dryland athletes. Submersion below the surface of water can provide sufficient pressure to backfill conventional microfluidic sweat sensors, resulting in disruption of the sweat analysis. High humidity environments can also cause false positives for hydration sensing in conventional water sensitive materials because they are not selective to only liquid water and are triggered by water vapor. Provided herein are devices, systems, methods and materials to facilitate sweat collection without false positives from a high-humidity or aquatic environment. Included are designs configured to prevent backfilling from the environment and for reducing the sensitivity of the hydration sensor to water vapor, thereby increasing overall sensitivity and minimizing risk of false readings or false positives.

Applications are wide-ranging, and include preventing environmental interference in the collection and analysis of sweat during aquatic exercise and preventing environmental interference in the collection and analysis of sweat during exercise in a humid environment.

The special configuration and designs provided herein offer a number of functional advantages, including: prevents backfilling from an aquatic environment; insensitive to humidity; and colorimetric hydration readout with high-contrast indicator.

A single, microfluidic outlet may provide air pressure relief as sweat enters the microfluidic channel via the single inlet laminated to the skin. Liquid water may be prevented from backfilling the sensor by virtue of small dimensions of the single outlet and the water contact angle at PDMS. In addition, a colorimetric hydration sensor may be used which is insensitive to humidity. The hydration sensor may be placed in chambers situated at various lengths along the channel to provide colorimetric readout of sweat loss to the user.

FIG. 1 Illustrates a microfluidic system having an inlet for introducing biofluid (e.g., sweat) to a microfluidic inlet conduit network. The microfluidic inlet fluidic network fluidically connects reservoir chambers positioned along a length of the network in a serial geometry. Capillary burst valves between each consecutive reservoir chamber, specifically between fluidically adjacent chambers, allows for the reservoir chambers to be filled with biofluid sequentially. Each reservoir chamber is fluidically connected to a circumferential microfluidic outlet conduit, which connects to a fluidic outlet, illustrated as a single microfluidic outlet configured to avoid unwanted backfilling. The liquid contact angle at the outlet and the outlet dimensions are such that liquid from a wet environment does not enter the microfluidic outlet conduit. The microfluidic system is designed to allow biofluid to enter through the inlet while not allowing liquid to enter at the outlet. Furthermore, colorimetric sensors may be positioned within the reservoir chambers. The colorimetric sensors are sensitive to a biofluid property and are insensitive to humidity.

Figure 2:
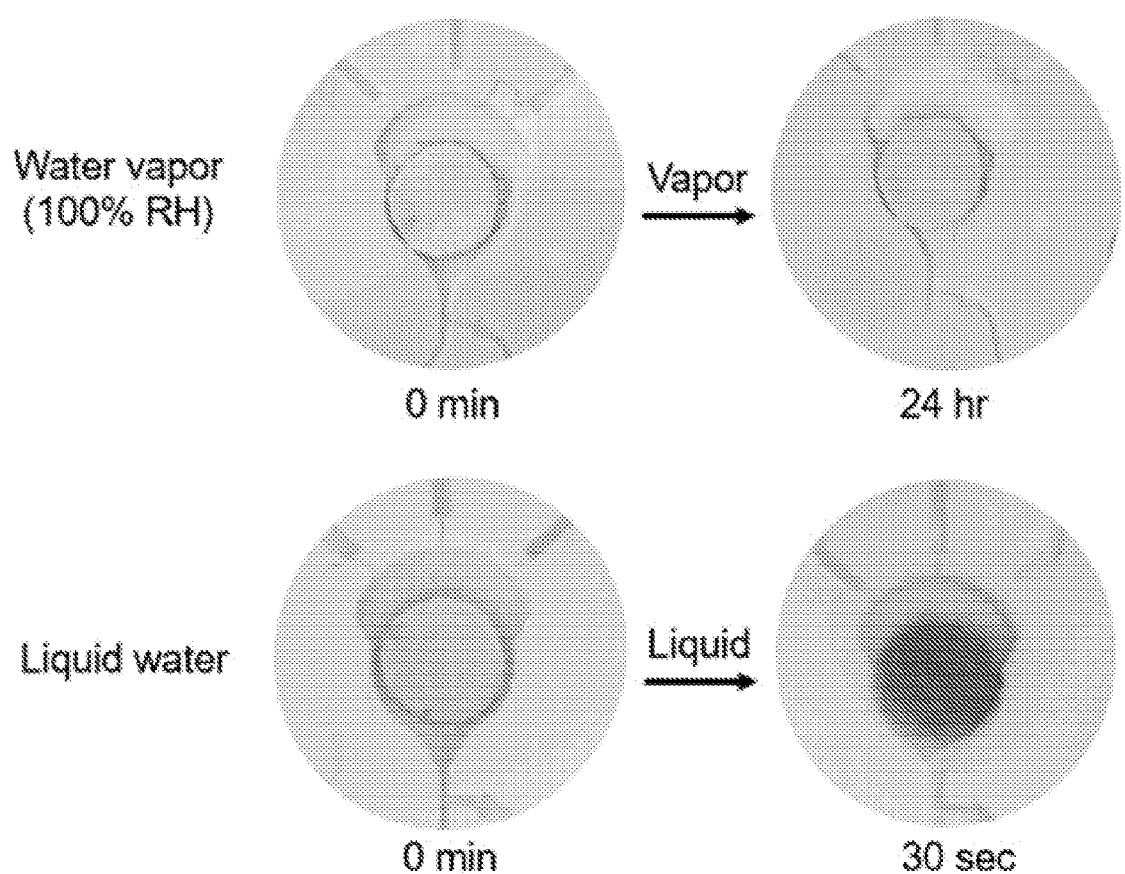
FIG. 2 illustrates an exemplary colorimetric sensor before (left) and after (right) exposure to humidity (top) or liquid water (bottom).

FIG. 2 illustrates an exemplary colorimetric sensor before (left) and after (right) exposure to humidity (top) or liquid water (bottom). Exposure to 100% RH water vapor for 24 hours has a negligible effect on the colorimetric sensor. Liquid water quickly changes the color of the sensor from white to red. This illustrates a colorimetric sensor that is insensitive to humidity.

Figure 3:
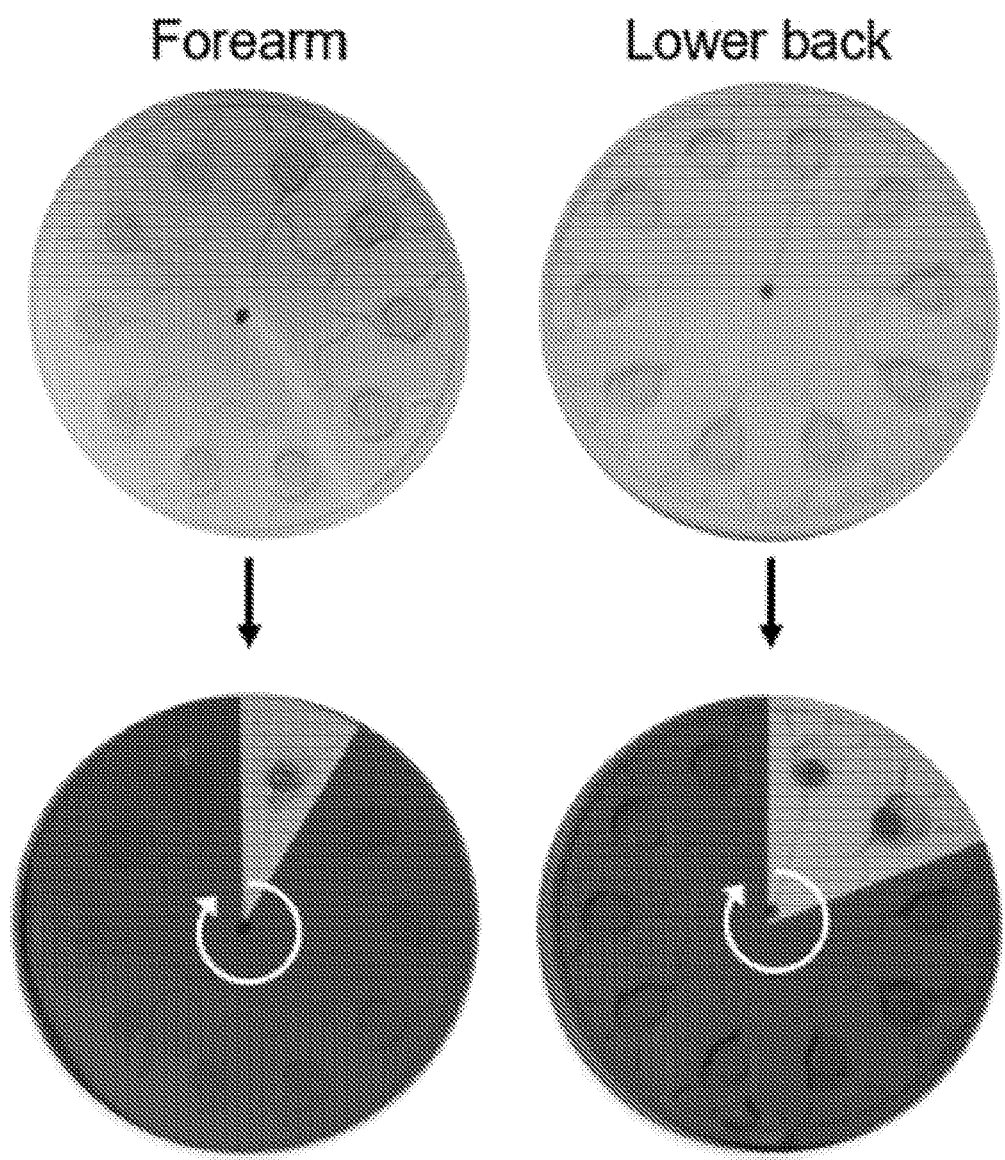
FIG. 3 illustrates an exemplary microfluidic system before (top) and after (bottom) use in a swimming pool.

FIG. 3 illustrates an exemplary microfluidic system before (top) and after (bottom) use in a swimming pool. A single chamber is filled on the forearm and two chambers filled on the lower back after approximately one hour of swimming. No backfilling or false positives are observed.

The thin geometries and soft mechanics of the devices disclosed herein allow for intimate and comfortable adherence to the skin for the purpose of collecting, manipulating, analyzing, and/or storing a biofluid, such as sweat, captured from aquatic athletes. The design may involve two layers of poly(dimethylsiloxane) (PDMS) supported on a medical-grade acrylic adhesive film for bonding to the skin. The first layer (e.g., substrate) may define a network of microfluidic channels, reservoir chambers, an inlet, an outlet, and capillary burst valves, such as illustrated in FIG. 1. For example, the channels may be 400 µm in thickness, and channel widths and heights may be 200 and 300 µm, respectively). The second layer may be a capping layer. For example, the capping layer may be in 200 µm thickness and may have a biofluid inlet aligned to the biofluid inlet of the first layer. The third layer may be an adhesive layer to establish adhesion to the skin and further define openings from which sweat can enter the microfluidic system. For example, the adhesive layer may be 50 µm in thickness and the openings in the adhesive layer may be 2 mm in diameter. For example, the microfluidic system illustrated in FIG. 1 consists of a network of microfluidic channels that connects to 10 separate chambers in parallel by bridging channels. Each chamber connects to an outlet opening (e.g., 0.5 mm diameter) designed to allow release of air that would otherwise be trapped in the chamber and serve as a source of backpressure to frustrate the filling of sweat into the chamber. PDMS is a good choice due to its dimensional stability in water, materials biocompatibility, low modulus, elastic mechanical properties, and compatibility with simple molding and bonding processes for fabrication.

FIGS. 2 and 3 depict example microfluidic systems disclosed herein before and after use. FIG. 2 depicts that the system is insensitive to humidity and responds only to liquid biofluid (liquid water in FIG. 2). FIG. 3 depicts that the system sequentially collects and monitors biofluid loss (e.g., sweat) from the skin surface over time. FIG. 3 further illustrates that the microfluidic systems may be placed on different parts of the body to monitor sweat rate, for example, on the different body parts.

EXAMPLE 2: CIRCULAR SERPENTINE EPIDERMAL MICROFLUIDIC SENSOR FOR SWEAT COLLECTION AND ANALYSIS FROM AQUATIC ATHLETES

This exemplary device consists of a waterproof combination of skin-like, or 'epidermal', microfluidic (epifluidic) and electronic systems that bond to the skin for capture, storage and chemical analysis of sweat, and for digital measurement of skin temperature, in aquatic and dryland environments. The platform incorporates microchannels, a chamber that houses a colorimetric chemical reagent, electronics for wireless communication and precision temperature sensing, a set of reference color markers and a skin-safe adhesive (FIG. 4A). A molded layer of poly(styrene-isoprene-styrene)

Figure 4F:
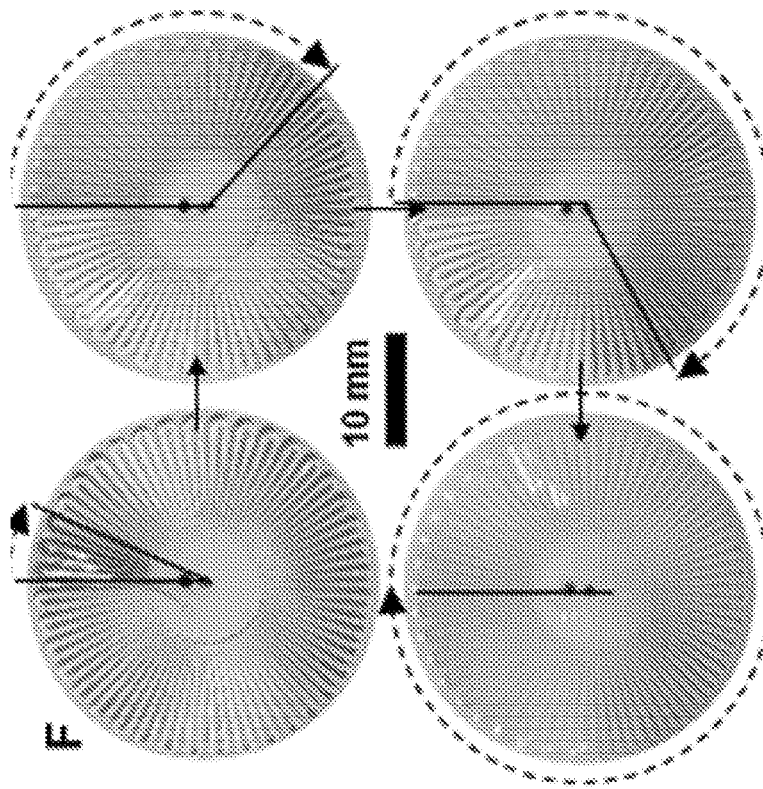
FIG. 4F provides a dye comprised of blue and red water-soluble particles which dissolve at different rates that result in a volume driven color change. Sweat volume collection is calculated by measuring the number of completed turns in the circular serpentine flow channel (1 turn=1.5 µL).

(SIS) bonded to a thin, flat sheet of SIS defines the sealed microfluidic system and also encapsulates the color markers (FIG. 4B). In the designs reported here, the microchannels have depths of ~220 μm in circular serpentine geometries with 40 turns, each of which has a capacity of 1.5 μL, for a total volume of ~60 μL. The colorimetric reagents consist either a food dye to facilitate visual assessment of extent of filling of the microchannel with sweat, or a silver chloranilate suspension to determine the concentration of chloride. This reagent resides in a chamber configured close to the inlet and is carried into the channel during sweat capture (FIG. 4D). The food dye includes red and blue water-soluble particles with different dissolution rates, to generate a volume-dependent color change as the device fills with sweat, as means to facilitate visualization. (FIG. 4F).

Figure 7E:
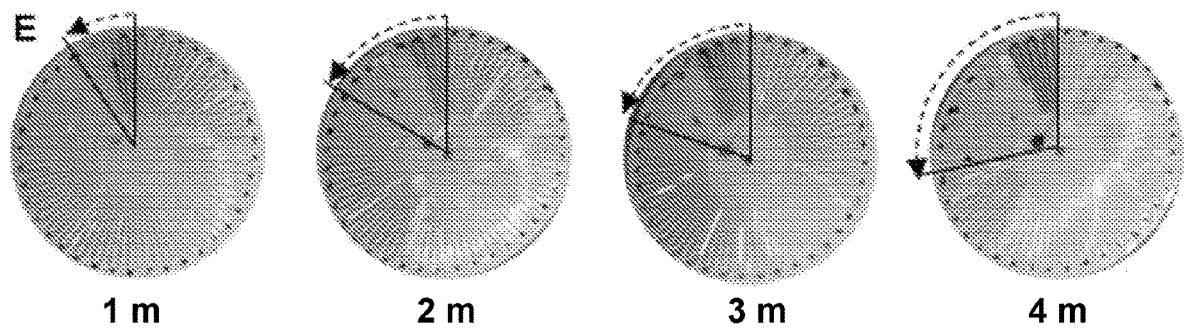
FIG. 7E the backfilling of the device in response to being submerged at various depths. Images were taken after remaining at depth for 10-15 s and then returning to the surface. Incomplete ejection of backfilled fluid after surfacing is likely due to changes in channel geometry after being subjected to high pressure and capillary forces.
Figure 7F:
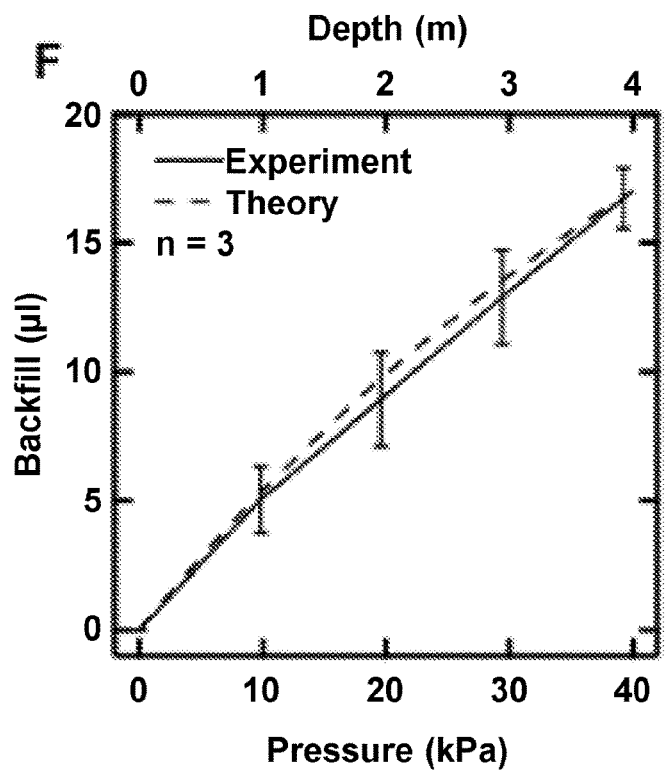
FIG. 7F compiled experimental and theoretical (ideal gas law) backfilling results.
Figure 8A:
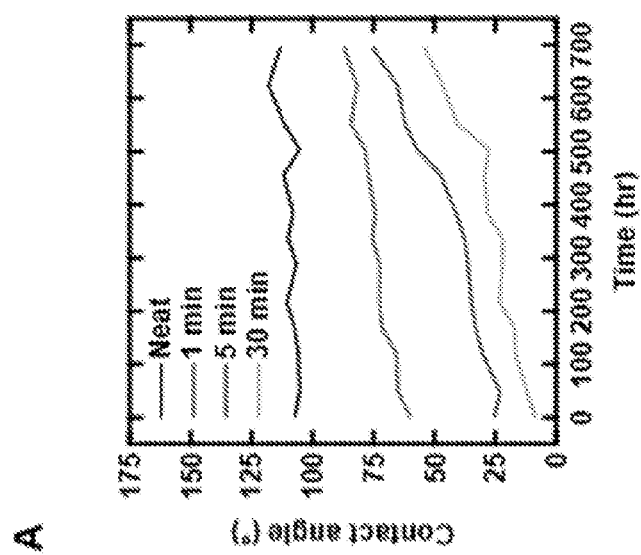
FIG. 8 shows aging of hydrophilic SIS rendered by UVO treatment FIG. 8A contact angle evolution in ambient air of SIS after treating with UVO for 1, 5 and 30 min.
FIG. 8B a neat SIS sample before and after 30 days of aging.
FIG. 8C an SIS sample treated with 30 min of UVO before and after 30 days of aging.
Figure 8B:
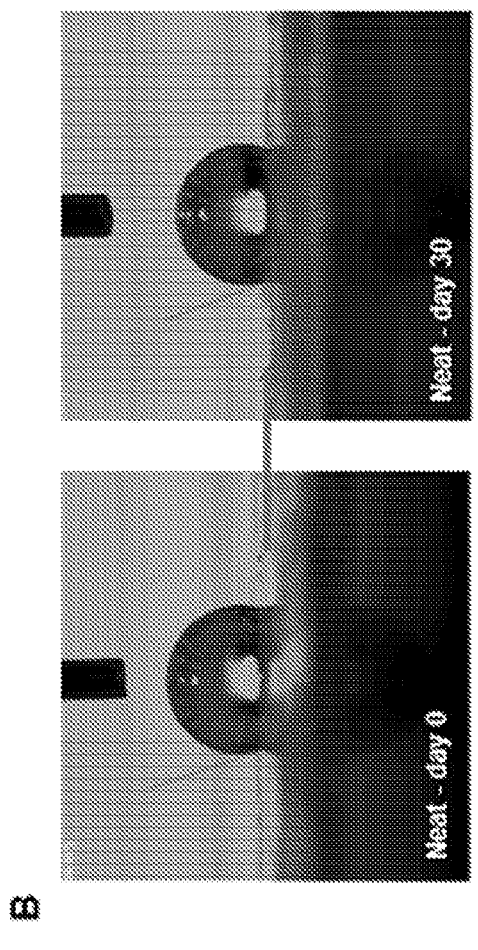
Figure 8C:
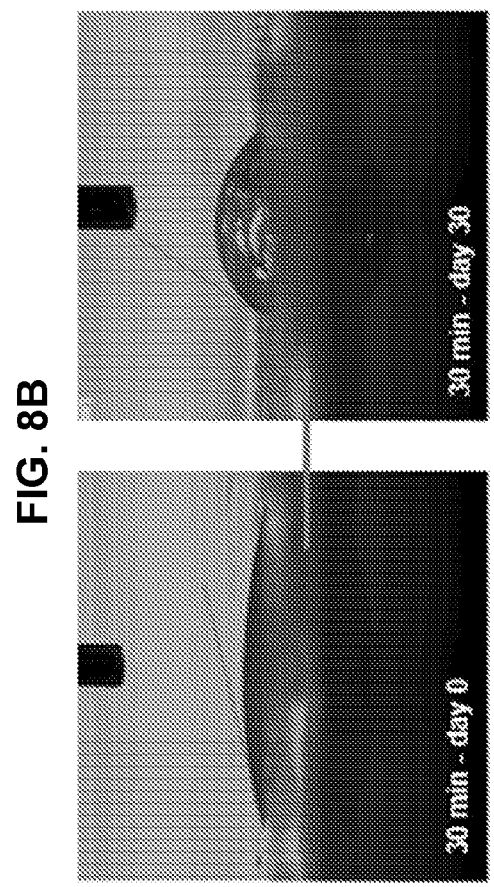

Reliable capabilities for collection of sweat during vigorous swimming and other aquatic activities, without ingress of water from the surroundings, follows from a combination of design attributes and materials properties, including 1) a microfluidic channel configuration that consists of a single, small outlet, 2) the low water permeability and water absorption properties of the SIS, 3) robust, watertight adhesion to the skin and 4) a small amount of "dead volume" near the outlet to accommodate pressure-induced backfilling. Regarding the fourth feature, the trapped air in the channel leads to volumes of backfill that are typically less than 2 μL for swimming near the surface of the water (FIG. 7). Contact angle measurements of SIS, as well as details on a method for rendering SIS hydrophilic via an ultraviolet light ozone treatment are in FIG. 8.

Figure 5H:
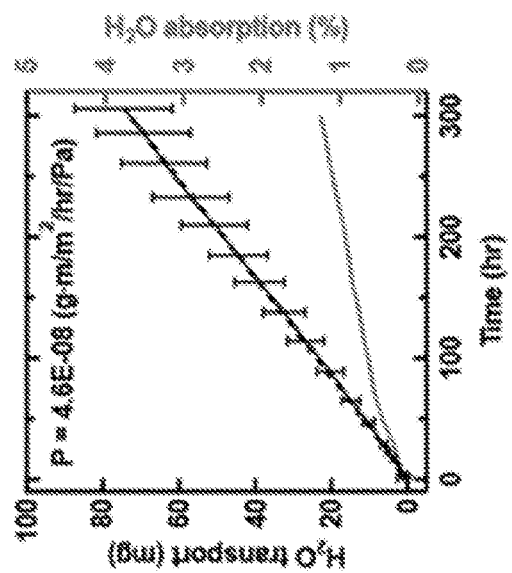
FIG. 5H is a graph providing SIS water absorption and water barrier properties.
Figure 5G:
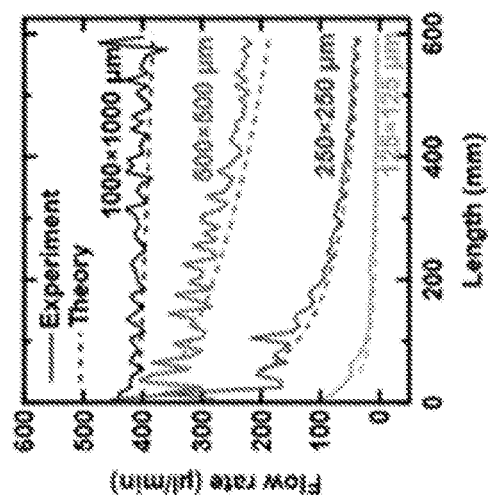
FIG. 5G is a graph showing geometry dependence of flow in the SIS microfluidic channels.
Figure 5F:
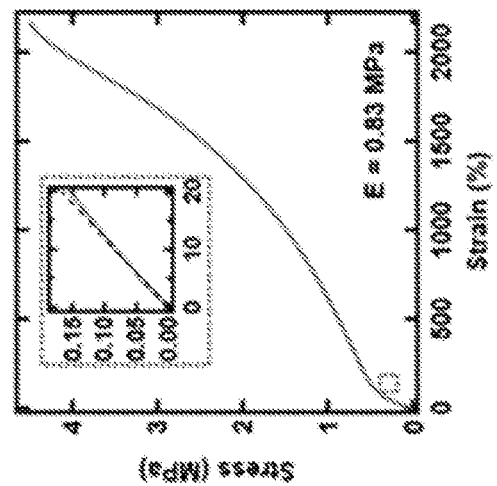
FIG. 5F is a graph showing stress-strain response of the SIS substrate.

Fabrication and characterization of SIS microfluidics: SIS offers a collection of physical characteristics that are useful for sweat collection in aquatic environments including hydrophobicity, resistance to water transport, optical transparency, low elastic modulus, and high elasticity. The layers of SIS that define the microfluidic structures follow from casting a solution of SIS in propyl acetate against flat silicon wafers and those with lithographically defined patterns of bas-relief, both with fluorinated surfaces to prevent adhesion. (FIG. 5A). The surface tension of the solution naturally creates a conformal coating on the bas-relief features as the propyl acetate evaporates (FIG. 5B). The high strain-to-failure exhibited by the SIS allows demolding of soft, intricate features without tearing. The stress/strain response of SIS in FIG. 5F illustrates the high strain-to-failure (>2000%) and low elastic modulus (E=0.83 MPa). Mechanically punching inlet and outlet holes in the bottom and channel layers, respectively, and laminating the two together (light pressure, contact for ~30 min) defines a waterproof bond to form the SIS microfluidic system. Mounting onto a skin-safe adhesive completes the fabrication (FIG. 5C). SIS exhibits excellent adhesion to itself and the skin adhesive without pre or post treatment. FIG. 5D shows a cross-sectional image of a representative region of a microfluidic channel, highlighting the contoured geometry of the top surface. The top layer of SIS consists of a ~150 μm thick conformal film with ~80 μm thick caps. As a result, the thickness of the SIS in between the channels is smaller than the height of the channel, thereby yielding a platform with thicknesses and corresponding bending stiffnesses that are much lower than those of previously reported systems. Cutting the top, molded SIS layer to a diameter of 32 mm and the bottom layer and adhesive to a diameter of 40 mm creates a 4 mm wide ring around the circumference that consists only of the bottom layer and adhesive. This tapered edge creates a low profile, conformal interface to the epidermis that also minimizes interface stresses near the edge. (FIG. 5E).

Figure 10:
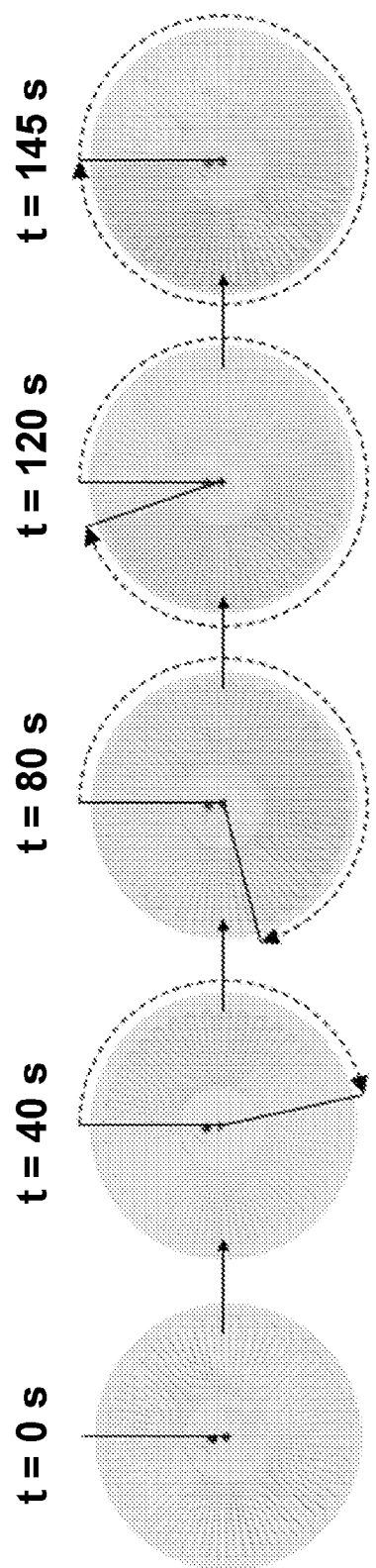
FIG. 10 shows filling rate at physiological sweat gland pressure. The progression of fluid through an epifluidic device at 2 kPa. The 60 μL device fill in 145 s, an average of 25 μL/min.

Minimizing sources of backpressure is critical to allow free, unimpeded flow of sweat into the device. The isobaric flow rate through a microfluidic channel is a function of the contact angle, surface tension, and channel geometry. The flow rates of water through SIS microchannels of various sizes at a pressure of 2 kPa, a physiologically relevant pressure for sweat glands [27], are summarized in FIG. 5G. Experimental details are in FIG. 9. The devices shown here have channel depths of ~220 μm and widths between 200 to 600 μm at the inner and outer radius, respectively. The 60 μL device fills in less than 2 min, with an average flow rate of 25 μL/min (FIG. 10). Physiological sweat rates range from 12-120 μL/hr/cm$^2$ [28], or 3-34 μL/hr from a collection area of r=3 mm. These designs, then, satisfy requirements for practical use. The overall results and the experimentally validated models serve as guidelines for future devices.

Reliable sweat collection in aquatic settings or in arid climates requires constituent materials with excellent barrier properties to prevent contamination or to eliminate evaporative loss, respectively. Results of measurements of water transport through SIS membranes and water absorption into bulk SIS appear in FIG. 5H. Less than 80 mg of water vapor passes through a 125 μm thick, 1.8 cm$^2$ SIS membrane over 12 days in a humid (>90%) environment (a permeability of $4.6 \times 10^{-8}$ g-m/mm$^2$/hr/Pa). SIS at 37° C. water absorbs less than 1.5% of its weight over the same period. Comparisons of evaporative loss of water from devices constructed in SIS and PDMS highlight the importance of barrier properties for collecting and storing sweat (FIG. 20). SIS devices with open outlets can store sweat at 37° C. for 4 hours with less than 20% loss while PDMS devices of comparable geometry lose ~100% within 3 hours.

Figures 6H, 6I, 6J:
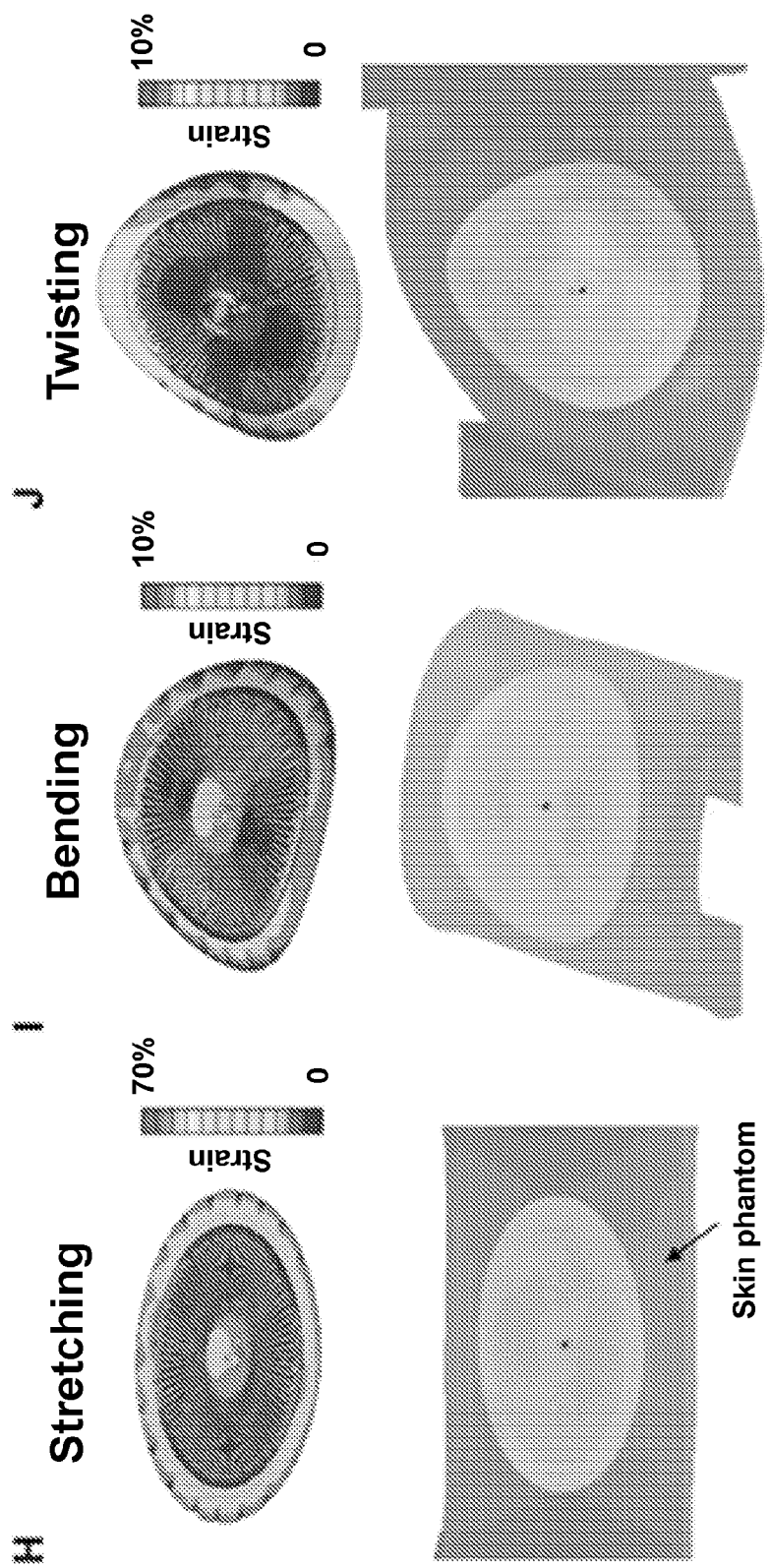
FIG. 6 provides the mechanics of conformal epifluidics.
FIG. 6A shows a device with a tapered edge on skin before and after wrinkling.
FIG. 6B illustrates delamination from the skin of a non-tapered device after wrinkling.
FIG. 6C Stretched.
FIG. 6D Compressed.
FIG. 6E Twisted.
FIG. 6F Pulled.
FIG. 6G shows a before and after of stretching to approximately 400%. Simulation and experiment of mechanical deformations are shown in FIG. 6H stretching (15%), FIG. 6I bending (r=3 cm) and FIG. 6J twisting (67.5°).1
Figure 11A:
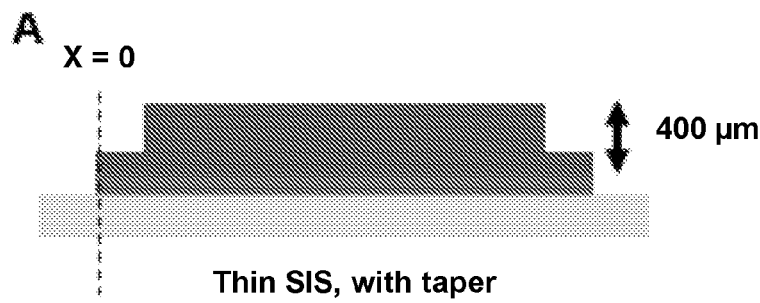
FIG. 11A provides a cross-sectional illustration for a 400 μm thick SIS device, with a tapered edge.
Figure 11B:
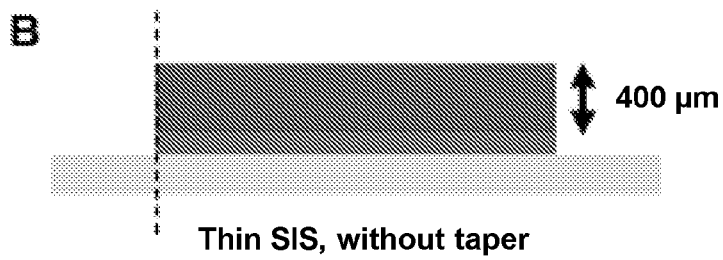
FIG. 11B provides a cross-sectional illustration for a 400 μm thick SIS device, without a tapered edge.
Figure 11C:
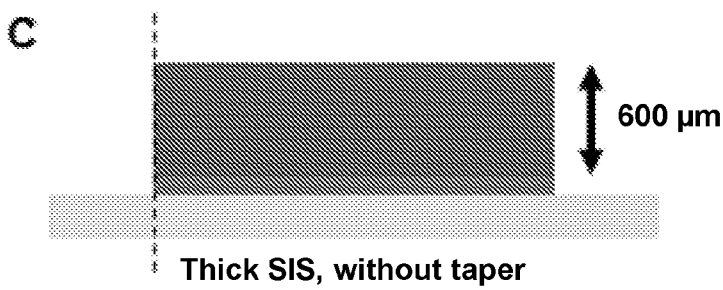
FIG. 11C provides a cross-sectional illustration for a 600 μm device, without a tapered edge.
Figure 11D:
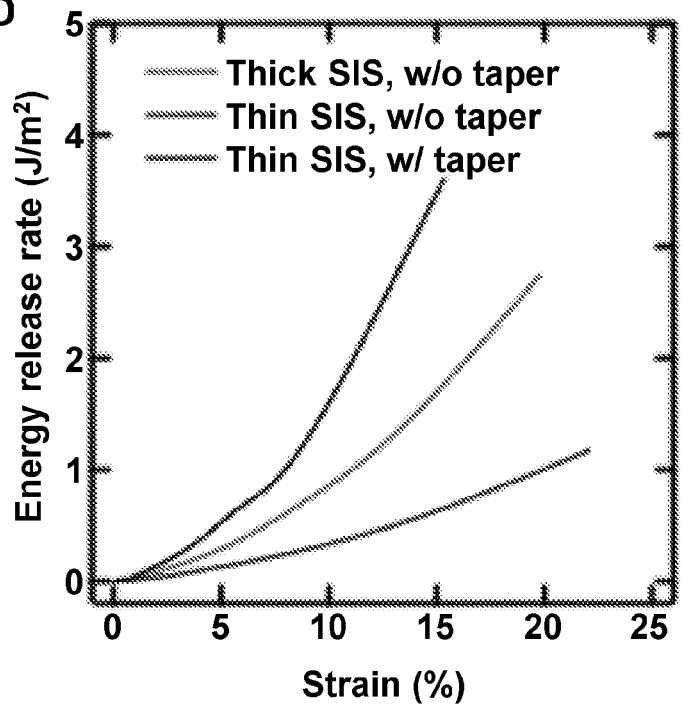
FIG. 11D provides modeling results for energy release rate of the three devices types provided in FIGS. 11A-C when straining up to 25%.
Figure 11E:
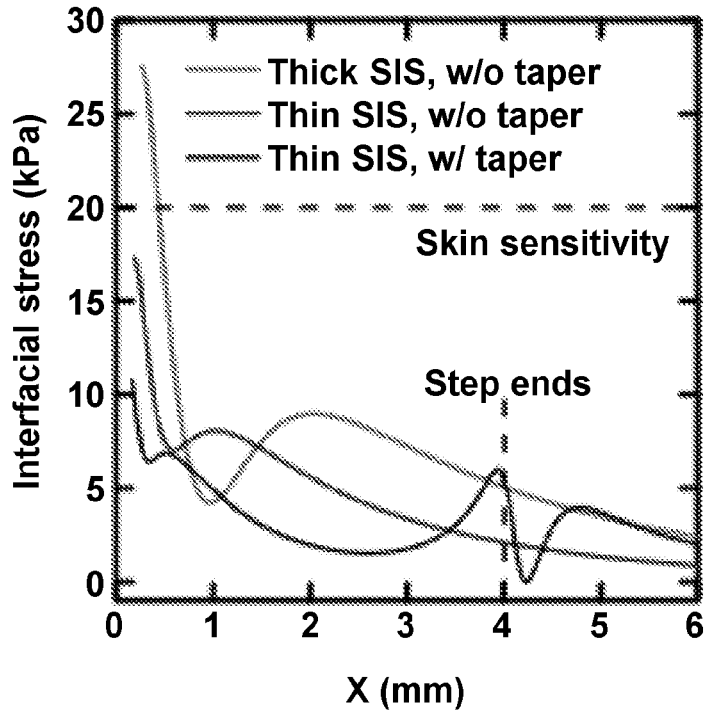
FIG. 11E provides modeling results for interfacial stress as a function of distance from the center of the three devices types provided in FIGS. 11A-C are stretched by 10%.
Figure 12B:
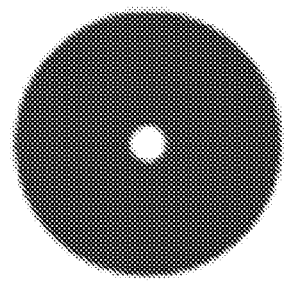
FIG. 12B Type 2 adhesive geometry with r=3 mm collection area.
Figure 12A:
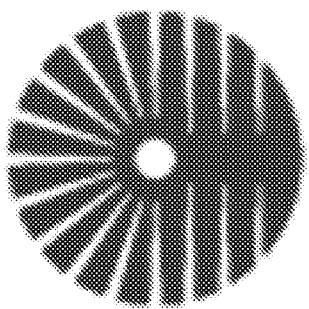
FIG. 12A Type 1 adhesive geometry with r=3 mm collection area and radial vents to decrease compensatory sweating. The non-symmetrical feature at the bottom enables easy removal of the adhesive backing.
Figures 12C, 12D:
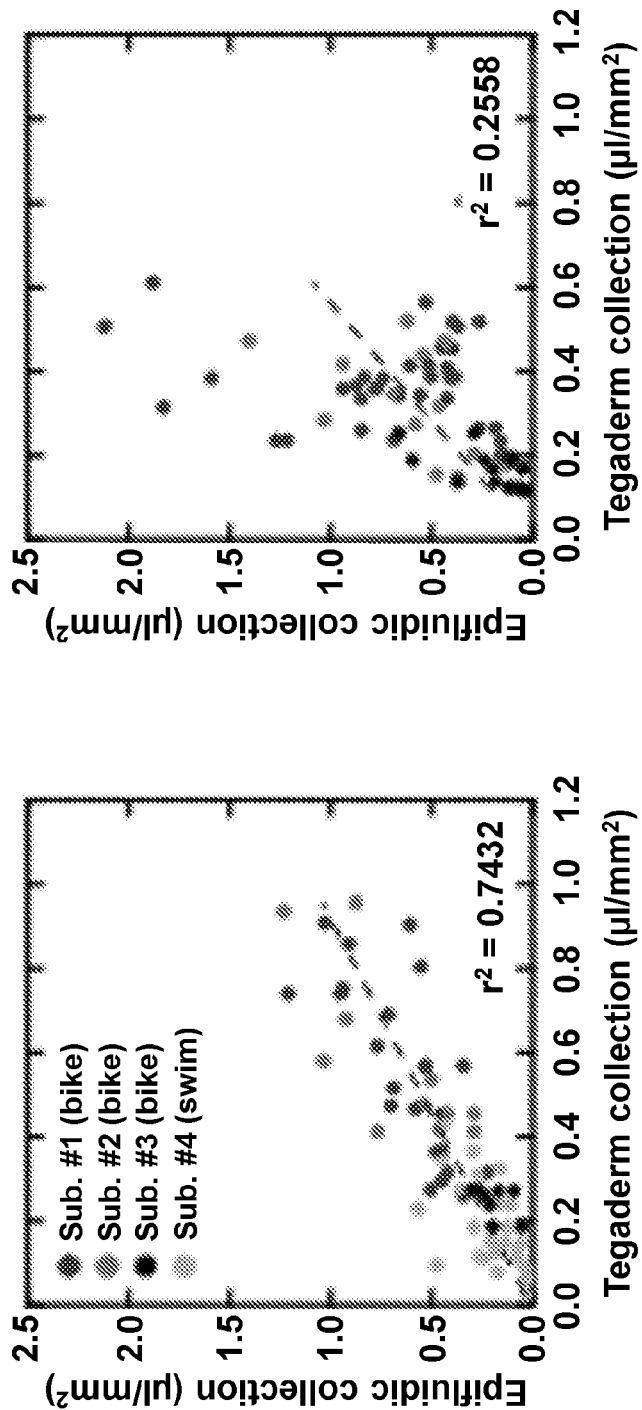
FIG. 12C-D provides the sweat volume collection of epifluidic devices with Type 1 and Type 2, respectively.
Figure 12F:
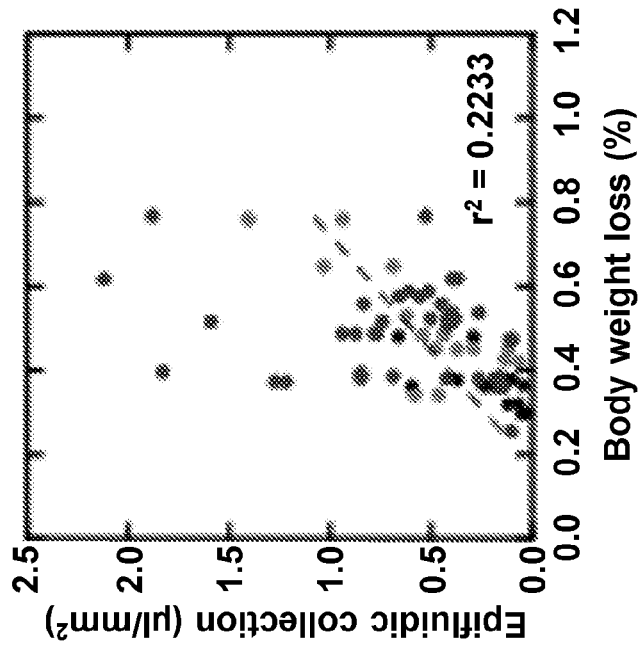
FIG. 12E-F show the volume collection of epidermal microfluidic devices with Type 1 and Type 2 adhesion, respectively, as compare to the percentage of body weight loss.
Figure 12E:
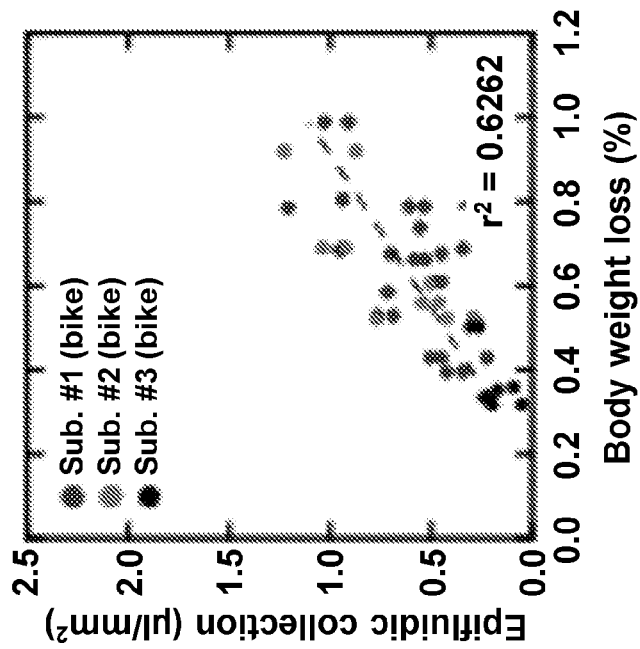
Figure 12H:
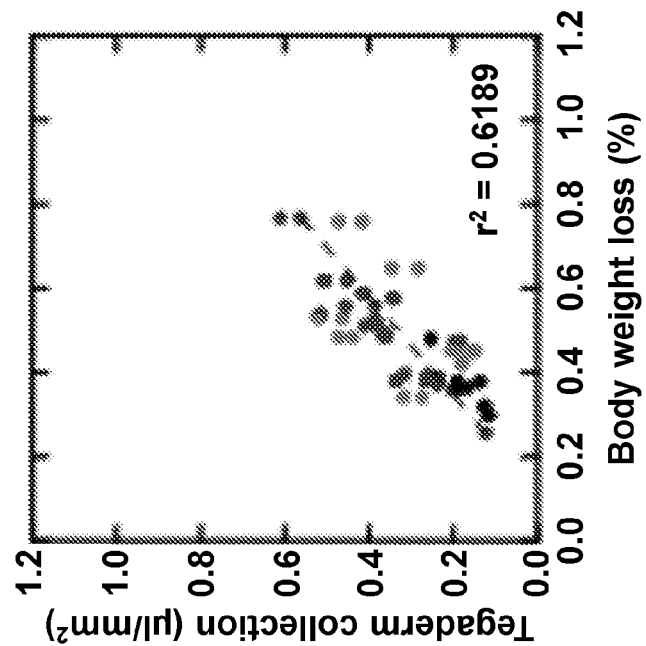
FIG. 12G-H show a comparison of sweat volume collected via absorbent pads to percentage body weight loss for the trials using the Type 1 and Type 2 adhesive, respectively.
Figure 12G:
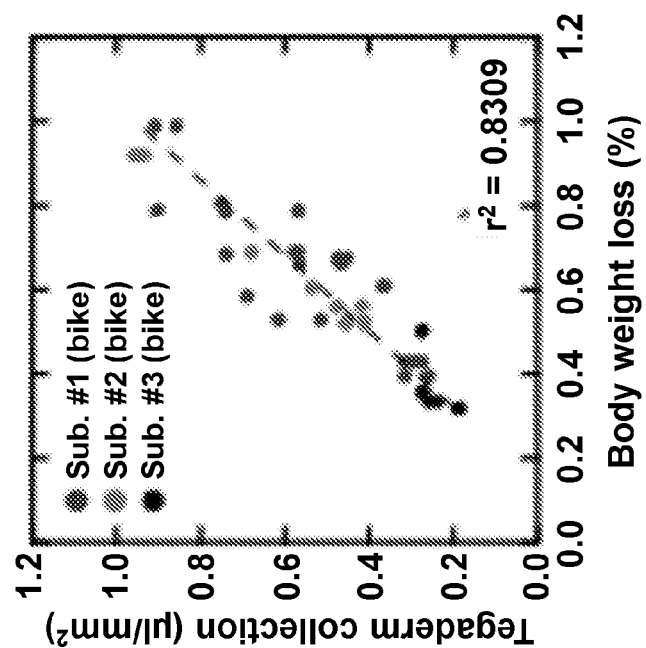

Mechanics of epidermal SIS microfluidics: Devices adhere conformally to the skin and present a low profile due to the thin geometry and tapered edge. Large deformations of the skin at the location of the device demonstrate the degree of conformality and robustness of adhesion during extreme deformations (FIG. 6A). Delamination results for similar deformations of devices that do not include the tapered edge (FIG. 6B). Results of mechanics modeling support this observation and quantify the reductions in energy release rates for thin devices with tapered edges compared to thick devices without a tapered edge (FIG. 11D). FIGS. 7C-F demonstrate the response to various natural movements. The low modulus and high elasticity enable large deformations, as in FIG. 7G. Finite element analysis (FEA) simulations of stress/strain distributions and respective photographs show various mechanical distortions for a device attached to a skin phantom of PDMS (FIG. 7H-J) The maximum stresses at the device/skin interface when the skin is stretched by 10% are well below the threshold for skin sensation (FIG. 11E).

Sweat collection and biomarker detection of aquatic and dryland athletes: Optimized choices for the device structure and the adhesive formulation, along with the favorable intrinsic properties of SIS, enable sweat collection in aquatic environments even during vigorous activities.

Robust, underwater adhesion follows from the low profile and tapered edge of the device, the low modulus of SIS and a strong, skin-safe adhesive. Collection of sweat from the skin without interference from an aquatic environment is enabled by the small diameter of the microfluidic outlet (r=0.25 mm), the high contact angle (110°) and barrier properties of the SIS. The skin adhesive forms a watertight seal, forcing sweat from the collection area to flow into the microchannel, which displaces the air in the channel into the aquatic environment. Water from the environment is prevented from entering the outlet due to the small dimensions of the channels and the hydrophobicity of the SIS. During intense swimming on the surface, water backfills less than 2 µl in the channel (FIG. 7). Hydrostatic pressure generated from diving can induce backfilling up to ~16 µL. Upon surfacing, the majority of this fluid is ejected due to the pressure of the trapped air in the channel. A small amount of fluid is unable to be ejected after surfacing, likely due to changes in the channel dimensions due to the high pressure (up to 40 kPa) and capillary forces.

Fabrication of ultrathin SIS microfluidic systems: Spin coating a 10 µm thick layer of negative photoresist (KMPR 1010) at 3000 RPM, 1000 RPM/s for 30 sec and soft baking at 110 °C. for 5 min prepared a silicon wafer for patterning. Exposure (420 mJ/cm2) through an iron oxide mask transferred the pattern into the photoresist. The wafer was hard baked at 110° C. for 5 min and developed in AZ 917MIF for 3 min. Deep reactive ion etch created trenches in the silicon wafer to a depth to 250 µm (STS Pegasus ICP-DRIE, SPTS Technologies Ltd.). Exposure to oxygen plasma (March CS-1701, 200W, 200 mT) for 15 min stripped the remaining photoresist. A fluorinated silane (trichloro(1H,1H,2H,2H-perfluorooctyl)silane, Sigma Aldrich) vapor deposited onto the patterned wafer by placing the it in a vacuum desiccator with 20 µL of the silane for 12 hrs formed a non-adhesive layer on the exposed silicon dioxide surfaces. Rinsing with IPA removed residual silane. Patterned and flat wafers underwent the same silane deposition process.

Dissolving 15 g of poly(styrene-isoprene-styrene) (14% styrene) (Sigma Aldrich) in 100 mL of propyl acetate (Alfa Aesar), with shaking periodically over a 24 hr period to ensure full dissolution, formed a solution for casting against a patterned silicon wafer. Mixing 2 wt % titanium dioxide powder (Sigma Aldrich) with the SIS solution and mixing in a planetary mixer (Thinky ARE-310) for 4 min at 2000 RPM yielded an opaque, white color. A PTFE-coated metal ring (Norpro 666) placed on the silanized, patterned wafer served to contain the solution at the edges. An 8 g sample of clear SIS solution formed the top, patterned layer. A 6 g sample of white SIS solution formed the bottom layer. Subsequent vacuum desiccation for 12 hrs served two purposes 1) to remove bubbles and 2) to provide a slow evaporation rate by maintaining a vapor bath around the SIS solution. The samples were dry to the touch after 12 hrs. Heating for 6 hrs at 80° C. on a hotplate removed any remaining solvent.

Fabrication of flexible NFC circuits and magnetic loop antennas: Laser structuring of a copper laminate (Pyralux AP8535R) by means of ablation (LPKF U4) formed flexible printed circuit boards (PCBs) for the NFC systems. Sonication in stainless steel flux, deionized water and IPA prepared the PCBs for mounting of active (AMS SL13A) and passive components (resistors, capacitors in 0201 package and blue LED (OSRAM 720-LBVH9GN1P2351Z) in 0402 package) using low temperature solder paste and a heat gun. Measurement of the resonant frequency of the NFC part of the circuit using a passive method (Keysight E4990A) confirmed the matched capacitance of the antenna and NFC chip, with adjustments as necessary via replacement of passive components. Dip-coating the completed device in a solution of SIS in propyl acetate (5 wt %) three times with a 30 s drying step in between coats formed a water-proof encapsulation.

Processes for assembling the devices: A circular steel punch (d=32 mm) and 0.5 mm steel punch defined the outer diameter and the outlet port for the molded SIS sheet, respectively. A 0.5 µL volume of colorimetric agent (food dye or silver chloranilate solution) filled the reaction chamber of the device. Americolor Soft Gel Paste, Violet, served as the food dye. The silver chloranilate solution consisted of 0.1 g of silver chloranilate (City Chemical) in 0.5 mL of 1 wt % aqueous poly(acrylic acid) (Sigma Aldrich). Sonicating this solution prior to application to the patterned, top layer ensured good dispersion. A $CO_2$ laser cutting system (Universal Laser, VLS3.50) formed the necessary patterns in a uniform sheet of skin adhesive (Scapa Unifilm U884). The white, bottom layer of SIS and the laser patterned adhesive encapsulated the SIS-coated NFC coil on the top and bottom, respectively. A 1 mm diameter steel punch created a hole for the inlet in the white SIS. Applying a color reference dial to the white SIS layer adjacent to the inlet facilitated direct colorimetric readout of the chloride level in the sweat with the naked eye or with cell phone camera and digital image processing. Lamination of the molded SIS layer with the reagent onto the flat, white layer of SIS encapsulated the color reference dial and reagent. Cutting the edges with a steel punch (d=40 mm) defined the outer perimeter of the device. Lightly pressing on the assembly for 30 min yielded a watertight bond between the microfluidic device layers.

Measurements of contact angle: Exposure of a sample of SIS to UV ozone (Jelight Model 144A) oxidized the surface. Each sample was prepared in triplicate. A VCA Optima XE contact angle measurement system enabled measurement of the evolution of the contact angle associated with 0.5 µL droplets of DI water.

Characterization of the mechanical properties: Tensile testing (MTS Sintech 20G) of samples of SIS in dogbone geometries (ASTM D1708) yielded the stress/strain relationships up across a range of strains from 0% to 2000%. A line fit between 0 and 10% strain yielded the Young's modulus. The strain rate was 20 mm/min.

Measurements of flow rates in microfluidic test structures: Tests of flow rate used molded SIS microfluidic structures with 61 cm long channels of various cross sections (125×125, 250×250, 500×500, 1000×1000 μm). Aluminum structures (6061) machined using a 3-axis mill (Roland MDX-540) served as the molds. Vacuum desiccation for 30 min removed bubbles from SIS cast in these molds and subsequently dried on a hot plate at 80° C. for 5 hr. A steel punch formed inlet and outlet holes (1 mm), and the molded layer was heat bonded to a flat SIS layer at 120° C. for 5 min. Mounting the sample to a Plexiglas holder with the device inlet aligned to a 2 mm aperture in the holder prepared the device for filling. A pressure-driven flow controller (Fluigent MFCS-EZ) pumped deionized water at 2 kPa through the aperture and into the device. A camera (Canon EOS Rebel T6i) placed above the device recorded the progression of the fluid through the channel. Extracting time points from the recorded video when the front of the flow passed 10 mm increments yielded the flow rate for each sample.

Measurements of water vapor penetration and absorption: Measurements of water vapor penetration and water adsorption followed the ASTM E96 and D860 protocols, respectively. Measuring the change in weight of a 20 mL scintillation vial filled with a desiccant and covered with a sheet of SIS yielded data on the rate of water vapor transmission. A 150 μm thick sheet of SIS sealed the mouth of the vial. Placing the vial and SIS sample in a sealed container with an open petri dish of water inside allowed testing in a humid environment. The humidity inside the sealed container was >95% and temperature was 20-25° C. Recording the increase in the mass of the vial periodically using a microbalance (Mettler ML204T) yielded the permeability of the SIS. Measuring the change in weight of puck-shaped pieces of SIS submerged in DI water yielded data on the rate of water absorption. A capped, scintillation vial filled with deionized water and stored in an oven at 37° C. formed an aqueous environment for the pucks (d=4 cm, thickness=2 mm). The samples were periodically removed from the vial, gently dried using a lint-free wipe, and weighed on a microbalance.

Filling SIS and PDMS devices with water and placing them in an arid environment (37° C., RH<10%) yielded data on the rate of evaporative water loss. A double-sided adhesive bonded the devices to a glass slide and ensured evaporative water loss occurred through only the top of the device. Each sample was weighed every hour using a microbalance. Tests were performed in triplicate.

Measurements of sweat loss in studies with human subjects: Measurements of % body weight loss (global loss) and mass gain of skin-mounted absorbent foam pads (local loss) provided two methods of comparison to the volume collected in the SIS epifluidic device. A body weight scale with 4 g precision (Adams GFK 330ah) enabled high precision measurements of % body weight loss before and after exercise while wearing either a swimsuit or underwear. Cleaning the application sites with an IPA wipe removed residual salts/oils and ensured good adhesion of the device. A rosin skin pretreatment (Gordon Labs, Stik-It) enhanced underwater adhesion during the Kona triathlete trials. Applying the pretreatment only to the skin underneath the adhesive prevented frustrating sweat glands in the collection area. After applying to the skin, pressure was applied for 10 s to ensure good adhesion. Absorbent foam pads (3M Tegaderm 3582) mounted nearby the SIS devices recorded local sweat loss. Weighing the absorbent pads immediately following the workout using a microbalance (Vibra 224R) produced the wet weight. Placing the pads in a 50° C. oven for 24 hrs evaporated the water before weighing again (dry weight). Weight due to skin oils, salt content, etc was assumed to be negligible. Subtracting the dry weight from the wet weight and dividing by the area of the absorbent pad (1000 mm$^2$) yielded the local sweat loss.

Measurements of skin temperature in studies with human subjects: The on-board temperature sensor of the AMS SL13A NFC chip enabled wireless skin temperature measurements. The AMS SL13A demo app on a Google Nexus 5X cell phone enabled untethered pairing and readout of the skin temperature. A handheld thermocouple reader with type-k thermocouple served as the reference temperature measurement. Recording skin temperature measurements every 500 m during swim trials yielded the time-evolution of the skin temperature. Quickly drying the measurement area with a towel before the NFC and reference measurements avoided spurious results due to water evaporation. Less than 15 s passed in between the swimmer reaching the pool wall and the measurements being taken. Skin temperature during biking was recorded in a similar manner, with the exception that the thermocouple remained taped to the skin using a skin-safe silicone adhesive tape.

Procedures for calibrating the chloride assay: Filling epifluidic devices containing the silver chloranilate reagent with 20 μL of known sodium chloride concentrations (25, 50, 75, and 100 mM) produced the reference color values for calibrating the chloride measurement. Imaging of the resulting product using a Canon EOS Rebel T6i DSLR camera with auxiliary LED lighting yielded the reference images. Lab color values were extracted from the images after correcting the white balance using a color checker (Spyder Checkr 24). The LAB color values from the images of the 25, 50, 75, and 100 mM concentrations formed the reference dial. Printing the reference dial on a 25 μm thick polyester sheet with adhesive backing (FLEXCon THERMLfilm SELECT 10852) using a commercial ink-jet printer enabled lamination onto the device. Verification of the reference colors was performed by repeating the calibration while using the color reference dial instead of correcting for white balance.

Measurements of sweat chloride levels in studies with human subjects: Devices containing the silver chloranilate reagent and an empty reference device were mounted on the midline of ventral forearm approximately 1 cm apart. Subjects swam for 45 min (~2500 m) or biked for 30 min (~14 km) and at least 15 μL of sweat was collected in the reference device. Imaging of devices using a Canon EOS Rebel T6i DSLR camera enabled extraction of the LAB color values in Photoshop. Converting the A and B color values using the calibration curve produced the chloride concentration measurement.

EXAMPLE 3: WATERPROOF NFC ELECTRONICS

Figure 4E:
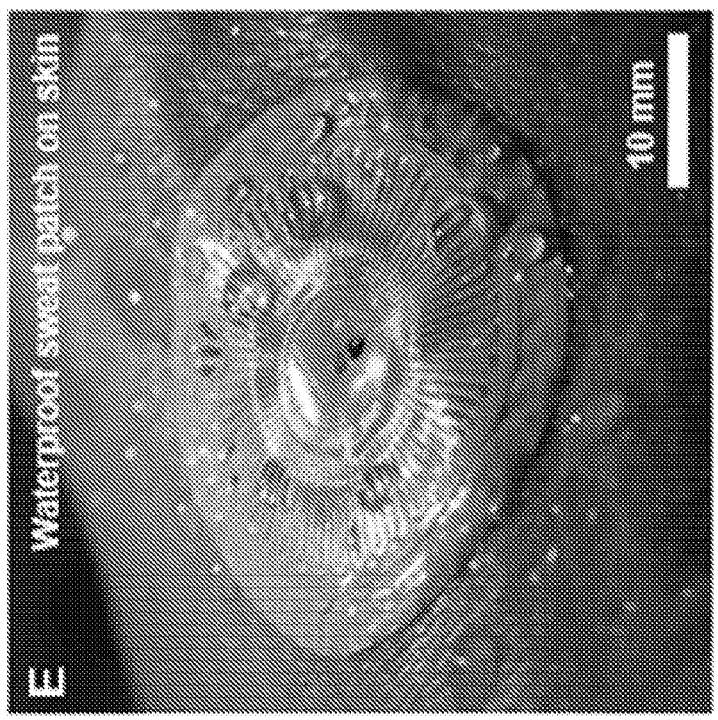
FIG. 4E provides sweat collection in aquatic environments which is enabled via the small size of the microfluidic outlet (r=0.25 mm) and contact angle of the SIS (110°). Dip-coating in SIS may enable underwater operation of the NFC coil and LED.
Figure 14:
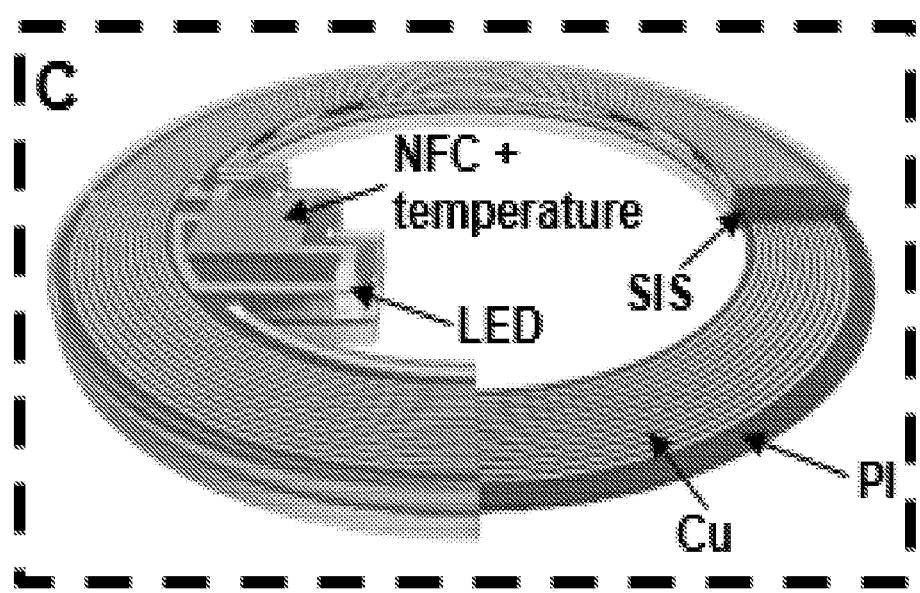
FIG. 14 provides an example of a waterproof near-field communication (NFC) device.
Figures 15A, 15B:
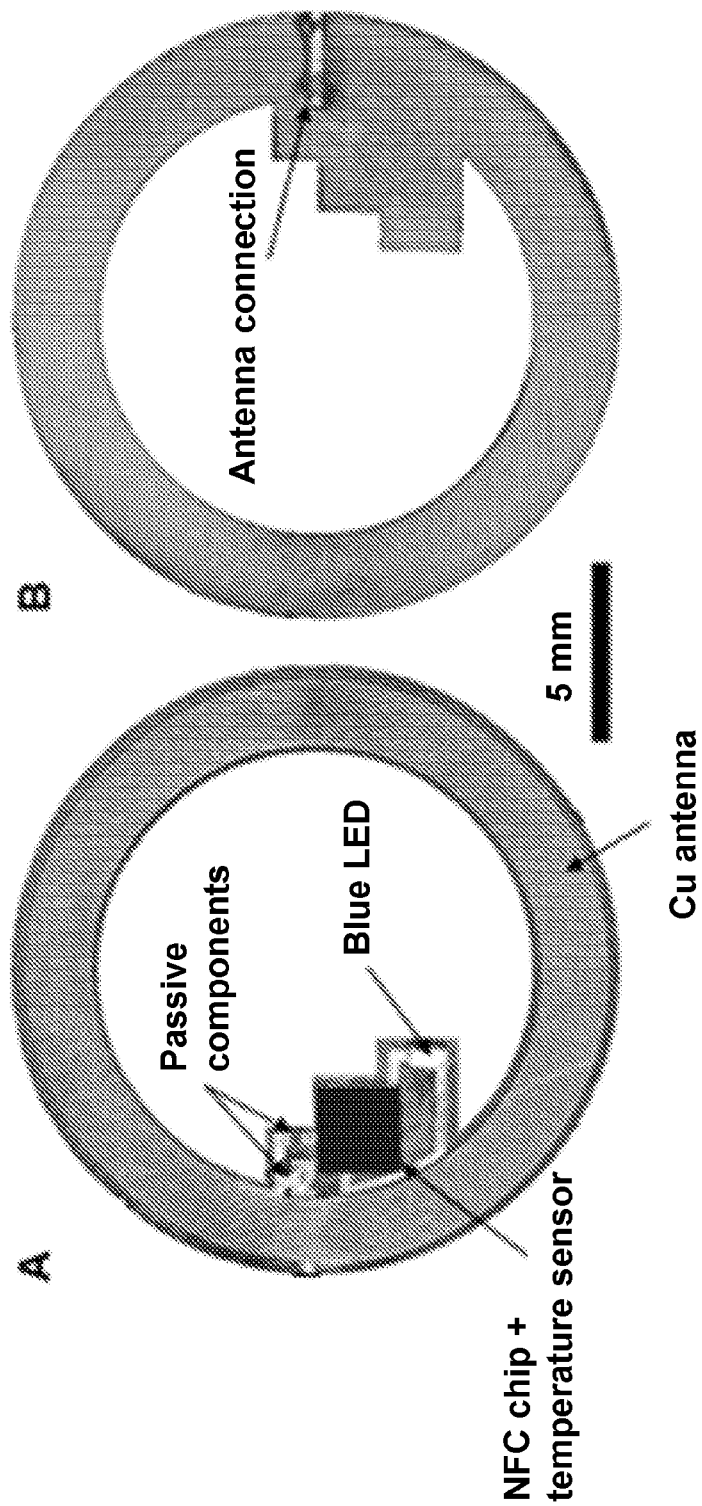
FIG. 15A Front side.
FIG. 15B Backside.
Figure 15C:
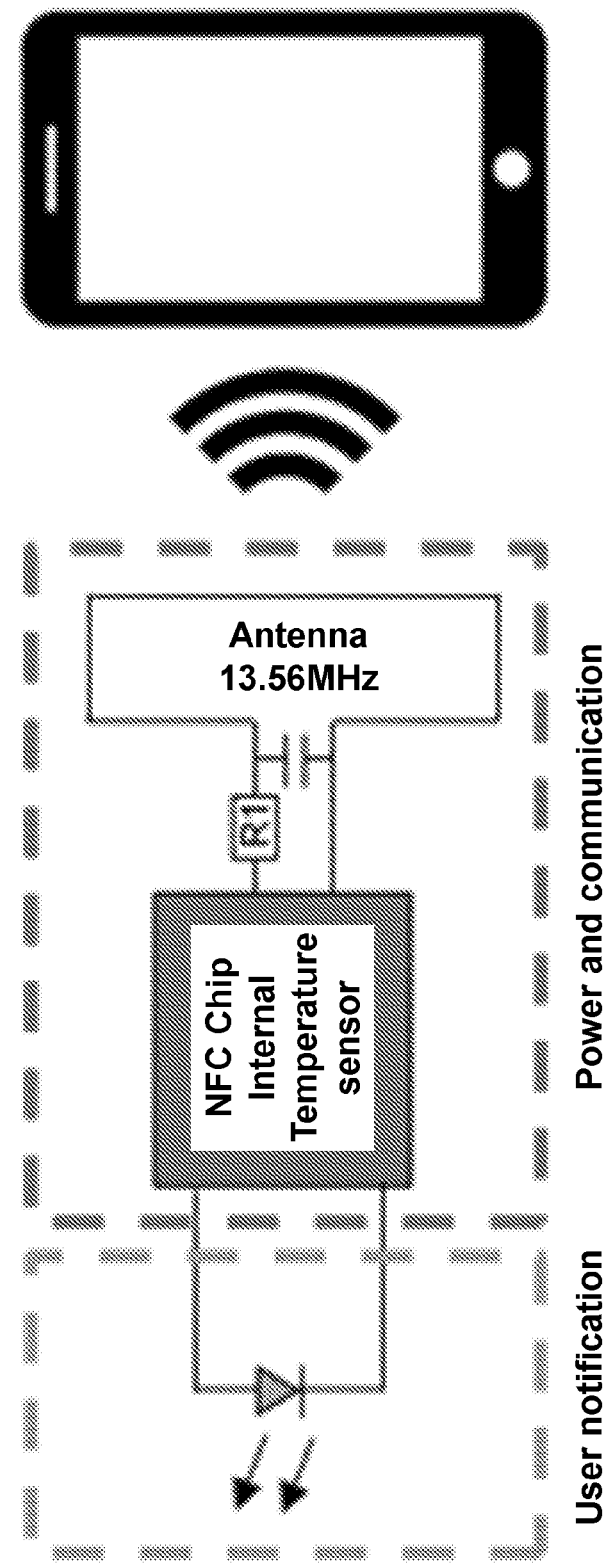
FIG. 15C provides a circuit diagram for skin temperature readout and user notification.

A flexible magnetic loop antenna, a set of near-field communication (NFC) components, and an LED as a mode for user notification form a wireless interface to NFC-enabled devices (smartphones, tablets, etc) for transmitting a digital identification code and a reading of skin temperature. Details on the processes for fabricating the NFC coil and on the circuit designs are in the methods and FIG. 15. A coating of SIS encapsulates the NFC electronics to allow robust operation for extended periods even when completely submerged in water (FIG. 14). FIG. 4E illustrates the wireless operation of the NFC electronics in a wet environment and shows the LED as it emits light through the microfluidic layers.

EXAMPLE 4: MEASUREMENT OF TOTAL SWEAT LOSS AND CHLORIDE LEVELS IN AQUATIC ATHLETES

Figures 16A, 16B, 16C:
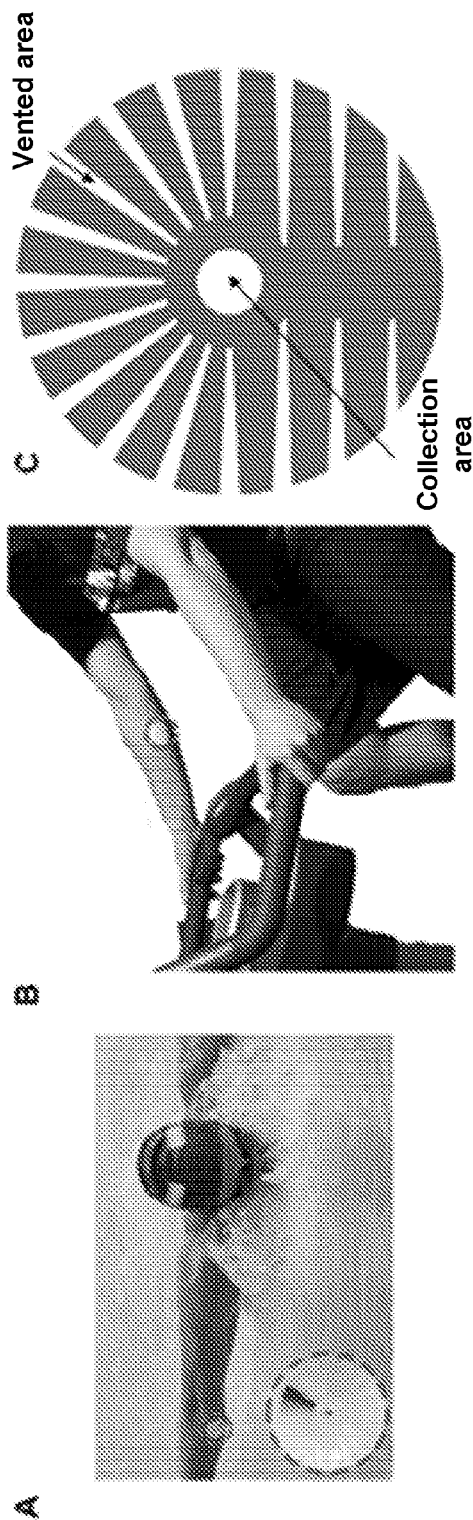
FIG. 16A A subject wearing an epifluidic device during a swimming study.
FIG. 16B A subject wearing an epifluidic device during a biking study.
FIG. 16C The sweat collection area is dictated by the adhesive geometry and is a circle with r=3 mm. Vents which extend radially from the center reduce the number of occluded sweat glands and compensatory sweating effect. This adhesive geometry is referred to as the Type 1 design.
Figure 16F:
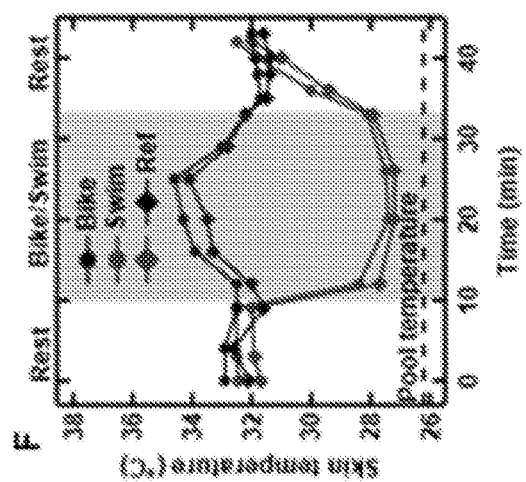
FIG. 16F Skin temperature during 25 min long swimming and biking sessions.
Figure 16E:
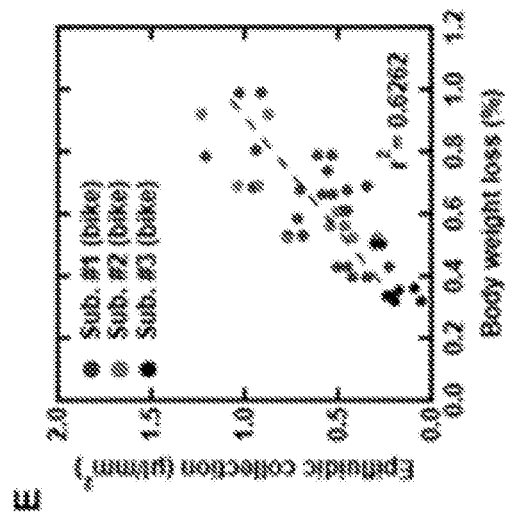
FIG. 16E Comparison of sweat volume collected via the epifluidic device vs. percentage body weight loss during biking.
Figure 16D:
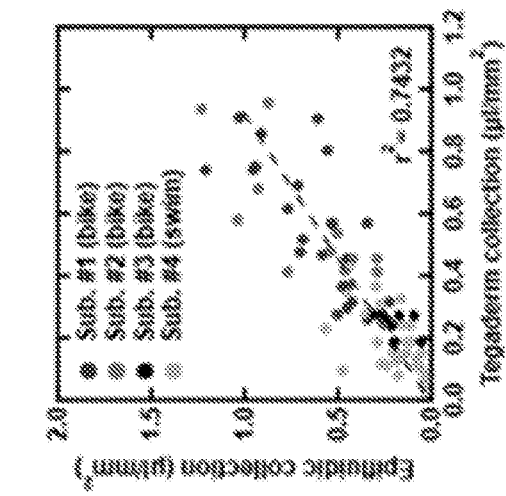
FIG. 16D comparison of sweat volume collected via the epifluidic devices vs. an absorbent pad during biking and swimming.

The device configuration described in this example allows measurements of the cumulative loss, the rate and the chloride concentration of sweat, via the microfluidic component of the system. The NFC component allows measurements of skin temperature. Photographs of two subjects wearing the device during swimming and biking are in FIG. 16A and 16B, respectively. Here, devices are on the midline ventral forearm, approximately 7 cm from the tip of the elbow. A laser-patterned skin-safe, acrylic adhesive bonds the device to the skin (referred to henceforth as the Type 1 adhesive) (FIG. 16C). Patterned openings reduce the area of occluded sweat glands by ~25%, thereby largely eliminating compensatory effects in sweat release that increase the local sweat rate due to occlusion of neighboring sweat glands, typically observed with unpatterned adhesive layers. The result improves the reliability and reproducibility of sweat collection. A comparison of sweat volume collected with the patterned (Type 1) and unpatterned (Type 2) appears in FIG. 12). Comparisons of results from a device with Type 1 adhesive to those obtained with a foam absorbent pad and to measurements of % body weight loss serve as validation against the two most common methods for measuring local and global sweat volume loss, respectively. The epifluidic data exhibit a good correlation ($R^2=0.74$) to results obtained with the absorbent pad for subjects who engaged in swimming and in biking (FIG. 16D). The sweat volume collected with the epifluidic device also correlates reasonably well with % total body weight loss ($R^2=0.63$, FIG. 16E). As a practical matter, reliable measurements of weight loss during swimming are not possible due to inadvertent, uncontrolled gain and loss of water (drinking water, etc).

Skin and core temperature both regulate sweating. The NFC temperature sensors built into the platforms described herein allow measurements of skin temperature of the forearm before, during, and after swimming and biking sessions (FIG. 16F). The data indicate that the skin temperature for the swimmer is initially ~34° C. and then drops to within 1-2° C. of the temperature of the pool water (26° C.) soon after entering the water. The temperature rises slightly after swimming for 25 min (1000 m) but remains within 2° C. of that of the pool. The skin returns to the initial temperature within 10 min of exiting the pool and drying off. The skin temperature of the biker rises shortly after beginning the exercise to reach a value of ~34° C. that then decreases in response to the evaporative effects of sweating. The skin temperature returns to initial values after ~5 min of rest.

Figures 16G, 16H:
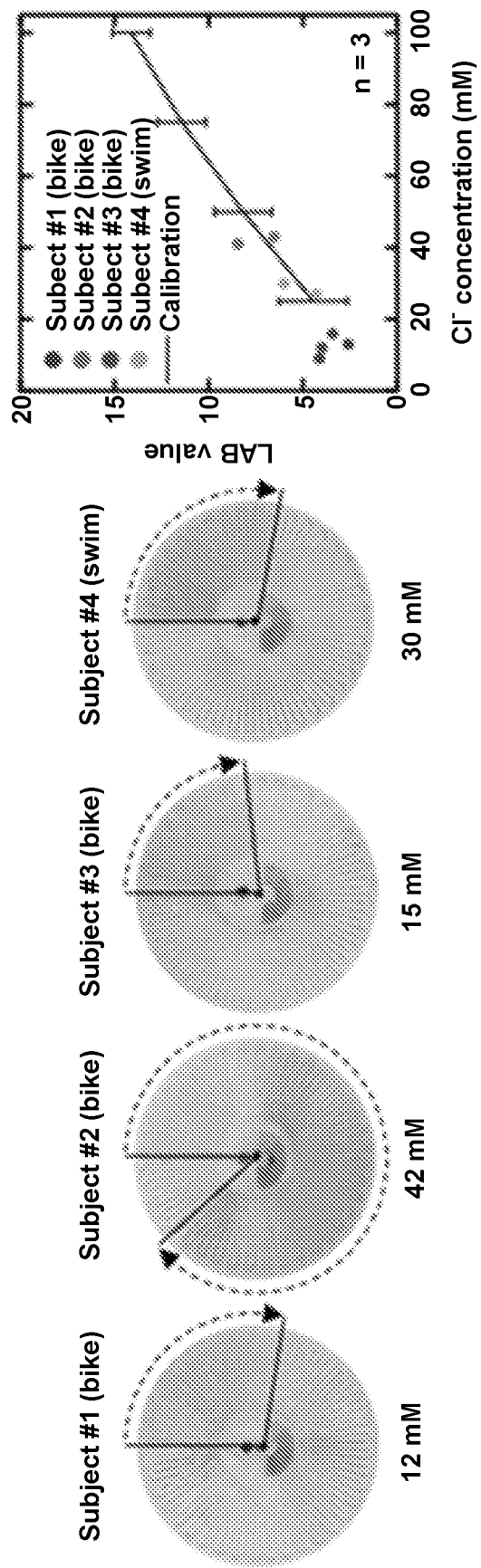
FIG. 16G Chloride measurements from swimming and biking exercise sessions.
FIG. 16H LAB color values of the chloride trials as compared to the chloride calibration curve.

Quantitative measurement of biomarkers in sweat collected in aquatic settings is possible by limiting the back-filling, and thus contamination, to the last ~3% of the channel by swimming on the surface. The chloride ion assay uses a reagent that changes color by an amount that quantitatively depends on chloride concentration. A fixed, printed color reference dial facilities visual readout. A linear correlation between chloride level and the LAB value (the projection of the measured a and b values onto the calibration curve) is observed. Subjects wore devices containing the chloride assay on the ventral forearm along with a reference device without the reagent for capturing sweat for post-trial measurement using a chloridometer. Devices imaged after subjects swam for 45 min (~2500 m) or biked for 30 min (~14 km) to collect at least 15 µL of sweat in the reference device from four subjects are shown in FIG. 16G, along with reference chloride values measured using a chloridometer. The chloride concentration in the pool was 18 mM. Color LAB values extracted from images of the devices after correcting for offsets in white-balance are plotted as a function of the reference chloride values in FIG. 16H. A calibration curve used for constructing the color reference dial is also shown. The results indicate an ability to measure chloride levels with approximately ±10 mM, sufficient to categorize into tertiles (i.e., low, medium, high). FIG. 13. Colorimetric measurements of chloride concentration with improved accuracy are possible with optimized microchannel geometries and color extraction algorithms.

Figures 17A, 17B, 17C:
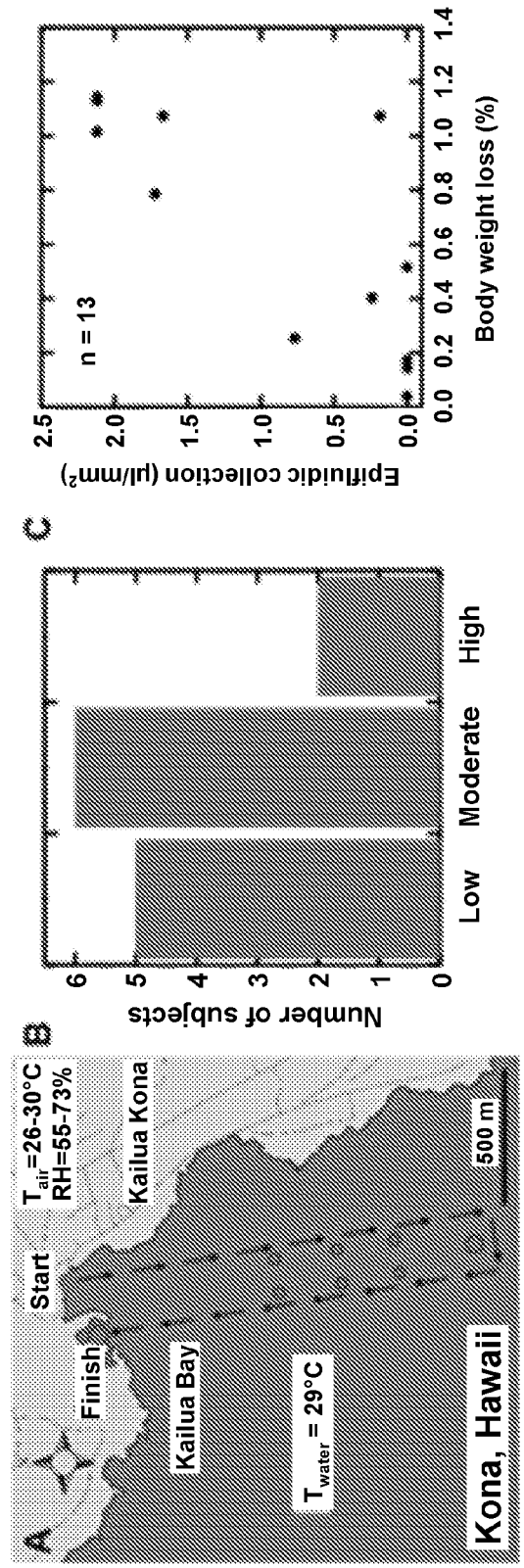
FIG. 17A A map of the route for the Kona swim trial.
FIG. 17B Self-reported swim intensity for the 13 subjects.
FIG. 17C Comparison of sweat volume collected during swimming via epifluidic devices vs. percentage body weight loss.
Figure 17D:
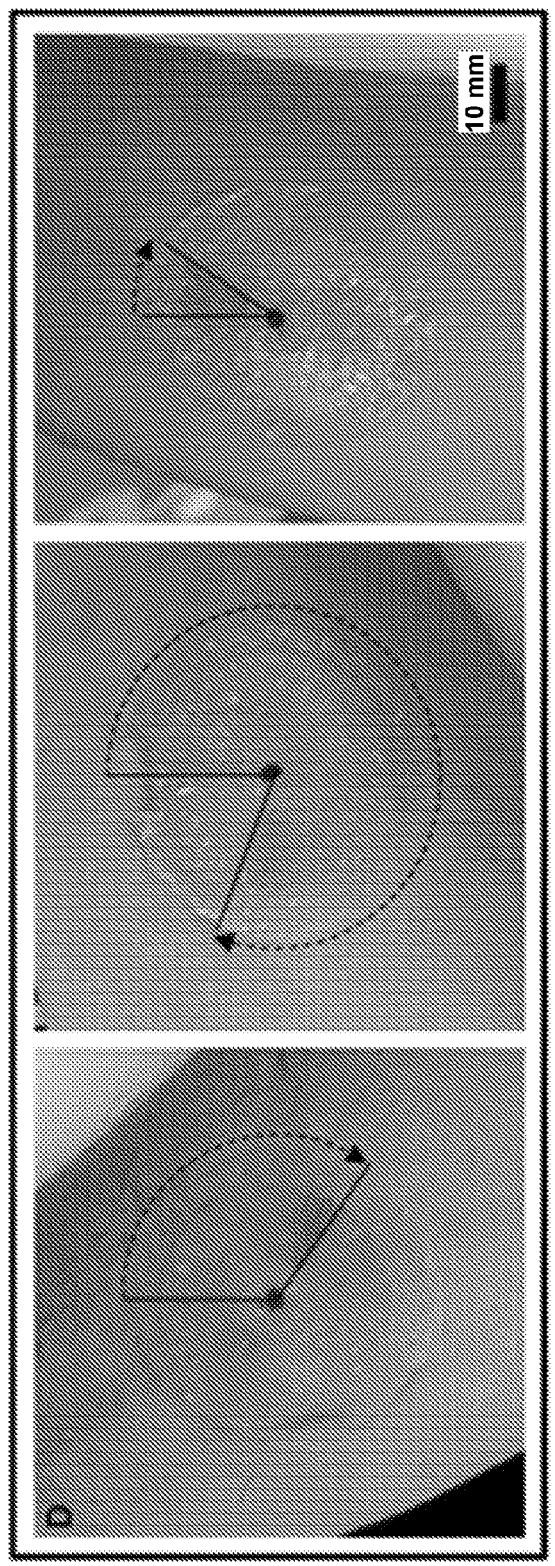
FIG. 17D representative images of epifluidic devices on three triathletes.

The performance evaluated in salt water demonstrates robust adhesion, proper filling and accurate operation in extreme environments. These studies involve epifluidic devices with the Type 2 adhesive worn by triathletes on the ventral forearm during practice swim sessions at the Ironman Championship. An illustrated map of the of the 3000 m long training route in the Kailua Bay in Kona, Hawaii is in FIG. 17A. Self-reported exertion levels from each athlete are in FIG. 17B. Local sweat loss recorded via the epifluidic device and % body weight loss show a positive correlation (FIG. 17C). Confounding changes in weight (e.g. drinking water) limit the utility of these comparisons. FIG. 17D shows representative photographs of three epifluidic devices after swimming.

Figure 18:
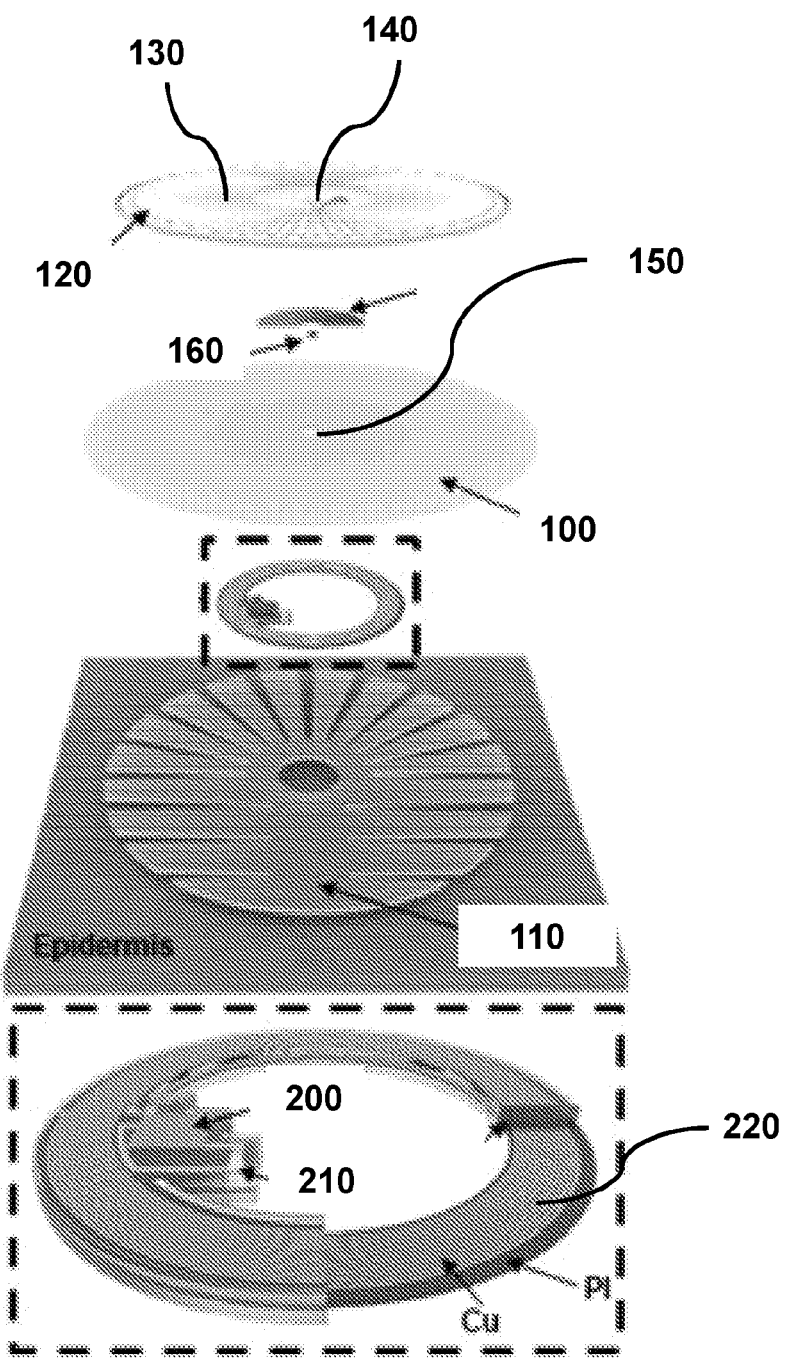
FIG. 18 provides a detailed schematic of an example microfluidic device.

FIG. 18 provides an example of a microfluidic device with a circular serpentine geometry, temperature sensor and NFC chip. The flexible substrate 100 is positioned between the adhesive layer 110 (which is proximate to the skin or epidermis) and the capping layer 120. In this example, the microfluidic inlet conduit network 130 is embedded in the capping layer 120 and has a circular serpentine geometry (see also FIG. 4B). The microfluidic outlet network 140, the biofluid inlet 150 and the colorimetric sensor 160 are positioned near the center of the device. The enlarged insert provides additional electronic components, including a temperature sensor 200, an LED 210 and a NFC coil 220.

Figure 19:
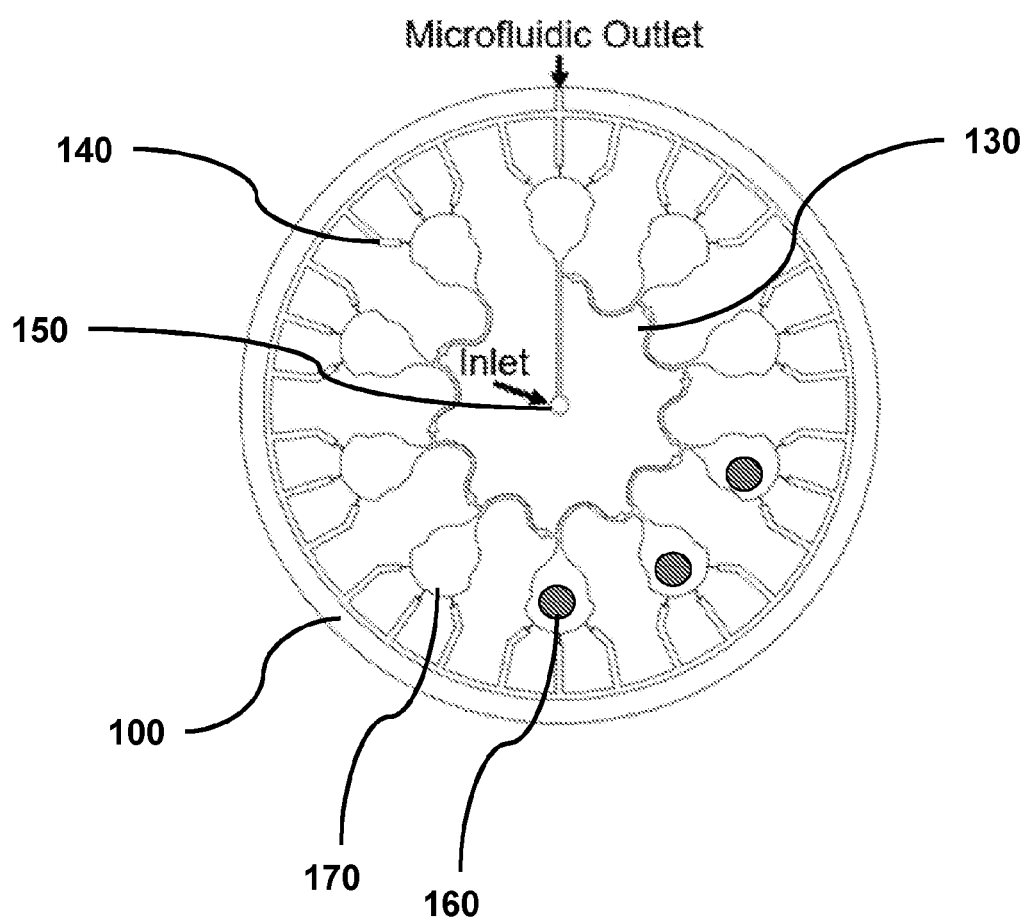
FIG. 19 provides a detailed schematic of an example microfluidic device with reservoirs.

FIG. 19 provides an example that utilizes reservoirs 170 embedded in the flexible substrate 100. The biofluid inlet 150 allows for the flow of biofluid into the microfluidic inlet network 130, which is further fluidically connected to each of the reservoirs 170. The reservoirs 170 each contain a colorimetric sensor 160 (not pictured in each reservoir). The microfluidic outlet network 140 is more complex than in the example provided in FIG. 18 as it must provide an outlet for each reservoir 170.

STATEMENTS REGARDING INCORPORATION BY REFERENCE AND VARIATIONS

All references throughout this application, for example patent documents including issued or granted patents or equivalents; patent application publications; and non-patent literature documents or other source material are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention. The specific embodiments provided herein are examples of useful embodiments of the present invention and it will be apparent to one skilled in the art that the present invention may be carried out using a large number of variations of the devices, device components, methods and steps set forth in the present description. As will be obvious to one of skill in the art, methods and devices useful for the present embodiments can include a large number of optional device components, compositions, materials, combinations and processing elements and steps.

Every device, system, combination of components or method described or exemplified herein can be used to practice the invention, unless otherwise stated.

When a group of substituents is disclosed herein, it is understood that all individual members of that group and all subgroups, including any device components, combinations, materials and/or compositions of the group members, are disclosed separately. When a Markush group or other grouping is used herein, all individual members of the group and all combinations and subcombinations possible of the group are intended to be individually included in the disclosure.

Whenever a range is given in the specification, for example, a number range, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. .

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein, any of the terms "comprising", "consisting essentially of" and "consisting of" may be replaced with either of the other two terms. The invention illustratively described herein suitably may be practiced in the absence of any element or elements and/or limitation or limitations, which are not specifically disclosed herein.

One of ordinary skill in the art will appreciate that compositions, materials, components, methods and/or processing steps other than those specifically exemplified can be employed in the practice of the invention without resort to undue experimentation. All art-known functional equivalents, of any such compositions, materials, components, methods and/or processing steps are intended to be included in this invention. The terms and expressions which have been employed are used as terms of description and not of limitation, and there is no intention in the use of such terms and expressions of excluding any equivalents of the features shown and described or portions thereof, but it is recognized that various modifications are within the scope of the invention claimed. Thus, it should be understood that although the present invention has been specifically disclosed by exemplary embodiments and optional features, modification and variation of the concepts herein disclosed may be resorted to by those skilled in the art, and that such modifications and variations are considered to be within the scope of this invention as defined by the appended claims.

It must be noted that as used herein and in the appended claims, the singular forms "a", "an", and "the" include plural reference unless the context clearly dictates otherwise. Thus, for example, reference to "a layer" includes a plurality of layers and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are described.

We claim:

1. An epidermal microfluidic system for use in a wet environment, the system comprising:
    a flexible substrate;
    a microfluidic inlet conduit network at least partially embedded in or supported by the flexible substrate;
    a biofluid inlet fluidically connected to the microfluidic inlet conduit network to provide a biofluid from a skin surface to the microfluidic inlet conduit during use;
    a microfluidic outlet conduit network fluidically connected to the microfluidic inlet conduit network and configured to relieve gas back pressure from the microfluidic inlet conduit network and sized to maintain liquid integrity of the system from the wet environment during use, wherein the microfluidic outlet conduit network comprises a biofluid outlet having a characteristic dimension selected to prevent liquid backfilling from the surrounding wet environment;
    at least one colorimetric sensor;
    a capping layer formed to cover a skin-facing surface of the flexible substrate and comprising a first auxiliary inlet aligned with the biofluid inlet, or formed to cover an outer-facing surface of the flexible substrate; and
    an adhesive layer comprising a second auxiliary inlet fluidically aligned with the biofluid inlet,
    wherein when the capping layer is formed to cover the outer-facing surface of the flexible substrate, the flexible substrate is positioned between the adhesive layer and the capping layer and the microfluidic inlet conduit network is embedded in the capping layer; and when the capping layer is formed to cover the skin-facing surface of the flexible substrate, the adhesive layer is positioned on at least a portion of an exposed surface of the capping layer.

2. The system of claim 1, further comprising:
a plurality of reservoir chambers, each reservoir chamber fluidically connected with the microfluidic inlet conduit network.

3. The system of claim 2, wherein the plurality of reservoir chambers is evenly distributed along a length of the microfluidic inlet conduit network in a serial configuration.

4. The system of claim 3, having a total microfluidic volume, wherein the plurality of reservoir chambers is at least 50% of the total microfluidic volume.

5. The system of claim 2, wherein the microfluidic inlet conduit network comprises a common inlet conduit with a plurality of inlet chamber conduits that fluidically connects each of the plurality of reservoir chambers to the common inlet conduit at a single connection.

6. The system of claim 5, wherein the microfluidic outlet conduit network further comprises a circumferential common outlet conduit having a plurality of chamber conduits that fluidically connects each of the plurality of reservoir chambers to the circumferential common outlet at a plurality of outlet connections.

7. The system of claim 6, wherein the plurality of chamber conduits is greater than or equal to 2 and less than or equal to 4.

8. The system of claim 7, wherein each of the plurality of chamber conduits connects to a chamber reservoir at a chamber constriction connection.

9. The system of claim 6, wherein the common inlet conduit is positioned in an interior region of the flexible substrate and the circumferential common outlet conduit is positioned in an exterior region of the flexible substrate, with the plurality of reservoir chambers extending between the common inlet conduit and the circumferential outlet conduit.

10. The system of claim 2, wherein said at least one colorimetric sensor comprises a plurality of colorimetric sensors positioned in fluidic communication with said microfluidic inlet network.

11. The system of claim 10, wherein each of the plurality of colorimetric sensors is positioned in a unique reservoir chamber to measure a biofluid property.

12. The system of claim 10, wherein each of the plurality of colorimetric sensors comprise a dye to indicate the presence of said biofluid in the plurality of reservoir chambers or said microfluidic inlet network.

13. The system of claim 10, wherein each of the of the plurality of colorimetric sensors comprise one or more color-responsive reagents for quantification of a biofluid volume or amount, flow rate, composition or any combination of thereof.

14. The system of claim 13, wherein the one or more color-responsive reagents are indicator reagents that react with liquid water, or with one or more analytes in said biofluid.

15. The system of claim 13, wherein at least one of the one or more color-responsive reagents is a silver chloranilate suspension.

16. The system of claim 13, wherein the color-responsive reagents are insensitive to humidity.

17. The system of claim 13, wherein the one or more color-responsive reagents are immobilized in a respective reservoir.

18. The system of claim 13, wherein the one or more color-responsive reagents are selected from the group consisting of dye, $CoCl_2$, glucose oxidase, peroxidase, potassium iodide, lactate dehydrogenase, diaphorase, formazan dyes, 2,4,6-tris(2-pyridiyl)-s-triazine (TPTZ) complexed with mercury ion or iron ion, a 2,2'-bicinchoninic acid, 1,10-phenanthroline, a universal pH indicator, silver chloranilate and any combination thereof.

19. The system of claim 2, wherein the microfluidic outlet conduit network maintains the liquid integrity of the system with the surrounding environment by preventing introduction of liquid into the plurality of reservoir chambers.

20. The system of claim 1, wherein the flexible substrate has a first diameter and the capping layer has a second diameter different from said first diameter of the flexible substrate.

21. The system of claim 20, wherein the second diameter of the capping layer is less than said first diameter of the flexible substrate.

22. The system of claim 21, wherein said second diameter of the capping layer is less than or equal to 90% of said first diameter of the flexible substrate.

23. The system of claim 1, wherein each of the flexible substrate and the capping layer independently comprise a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, polyvinyl chloride, poly(styrene-isoprene-styrene), chitosan, and any combination thereof.

24. The system of claim 23, wherein at least one of the flexible substrate and the capping layer is poly(styrene-isoprene-styrene).

25. The system of claim 1, wherein the adhesive layer comprises medical grade acrylic.

26. The system of claim 1, wherein the flexible substrate has an average thickness selected from the range of 500 μm to 2 mm, wherein the capping layer has an average thickness selected from the range of 50 μm to 1 mm, and wherein the adhesive layer has an average thickness selected from the range of 10 μm to 100 μm.

27. The system of claim 1, wherein said at least one colorimetric sensor is a dye in fluidic communication with said microfluidic inlet network.

28. The system of claim 27, wherein at least a portion of said dye is mixed with said biofluid when said biofluid enters said microfluidic inlet network, thereby providing a visual indication of fluid flow through said microfluidic inlet network.

29. The system of claim 1, wherein said biofluid outlet has a cross-sectional area less than or equal to 0.6 $mm^2$.

30. The system of claim 1, wherein the biofluid inlet has a characteristic dimension configured to facilitate a biofluid entry to the microfluidic outlet conduit network.

31. The system of claim 30, wherein the biofluid inlet has a cross-sectional area that is greater than or equal to 1 $mm^2$.

32. The system of claim 1, wherein each of one or more cross-sectional areas of the microfluidic outlet conduit network is selected from the range of 0.1 $mm^2$ to 0.3 $mm^2$.

33. The system of claim 1, wherein the microfluidic inlet conduit network collects at least a portion of said biofluid released from a skin surface via capillary action, a pressure differential or a combination of thereof.

34. The system of claim 1, wherein the microfluidic inlet conduit network has a circular serpentine geometry.

35. The system of claim 34, wherein said serpentine geometry has a number of turns or loops greater than or equal to 25, wherein each of said turn or loop has a volume less than or equal to 5 μm.

36. The system of claim 1, wherein the microfluidic inlet conduit network has a depth of less than or equal to 500 μm and a width selected from the range of 100 μm to 800 μm.

37. The system of claim 1, further comprising at least one of a temperature sensor, a wireless device, and at least one light emitting diode (LED).

38. The system of claim 37, wherein said temperature sensor is embedded in or supported by the flexible substrate and provides a body temperature of a wearer of the system.

39. The system of claim 37, wherein said wireless device is a transmitter, a receiver or both.

40. The system of claim 37, wherein said wireless device is a near-field communication (NFC) coil.

41. The system of claim 37, wherein said wireless device is wirelessly powered.

42. An epidermal microfluidic system for use in a wet environment, the system comprising:
- a flexible substrate;
- a capping layer supported by the flexible substrate; wherein the capping layer has a diameter less than that of the flexible substrate, thereby forming a tapered geometry;
- a microfluidic inlet conduit network having a circular serpentine geometry at least partially embedded in or supported by the flexible substrate, the capping layer or both the flexible substrate and the capping layer;
- a biofluid inlet fluidically connected to the microfluidic inlet conduit network to provide a biofluid from a skin surface to the microfluidic inlet conduit during use;
- a microfluidic outlet conduit network fluidically connected to the microfluidic inlet conduit network and configured to relieve gas back pressure from the microfluidic inlet conduit network and sized to maintain liquid integrity of the system from the wet environment during use, wherein the microfluidic outlet conduit network comprises a biofluid outlet having a characteristic dimension selected to prevent liquid backfilling from the surrounding wet environment; and
- a dye in fluidic communication with the microfluidic inlet conduit network, wherein said dye mixes with said biofluid upon entry of the microfluidic inlet conduit network, thereby providing a visual indicator of the flow of said biofluid through the microfluidic inlet conduit network,.
- wherein each of the flexible substrate and the capping layer independently comprise a material selected from the group consisting of polydimethylsiloxane (PDMS), polyurethane, cellulose paper, cellulose sponge, polyurethane sponge, polyvinyl alcohol sponge, silicone sponge, polystyrene, polyimide, SU-8, wax, olefin copolymer, polymethyl methacrylate (PMMA), polycarbonate, poly(styrene-isoprene-styrene), chitosan, and any combination thereof.

43. The system of claim 42, further comprising a temperature sensor embedded in or supported by the flexible substrate, wherein said temperature sensor provides a body temperature of a wearer of said system.

44. The system of claim 42, further comprising an NFC coil embedded in or supported by the flexible substrate.

45. A method for measuring a biofluid property, comprising:
providing an epidermal microfluidic system comprising:
- a flexible substrate;
- a microfluidic inlet conduit network at least partially embedded in or supported by the flexible substrate;
- a biofluid inlet fluidically connected to the microfluidic inlet conduit network to provide a biofluid from a skin surface to the microfluidic inlet conduit during use;
- a microfluidic outlet conduit network fluidically connected to the microfluidic inlet conduit network and configured to relieve gas back pressure from the microfluidic inlet conduit network and sized to maintain liquid integrity of the system from a wet or aquatic environment during use, wherein the microfluidic outlet conduit network comprises a biofluid outlet having a characteristic dimension selected to prevent liquid backfilling from the surrounding wet or aquatic environment; and
- at least one colorimetric sensor;
- a capping layer formed to cover a skin-facing surface of the flexible substrate and comprising a first auxiliary inlet aligned with the biofluid inlet, or formed to cover an outer-facing surface of the flexible substrate; and
- an adhesive layer comprising a second auxiliary inlet fluidically aligned with the biofluid inlet,
- wherein when the capping layer is formed to cover the outer-facing surface of the flexible substrate, the flexible substrate is positioned between the adhesive layer and the capping layer and the microfluidic inlet conduit network is embedded in the capping layer; and when the capping layer is formed to cover the skin-facing surface of the flexible substrate, the adhesive layer is positioned on at least a portion of an exposed surface of the capping layer;
mounting said epidermal microfluidic system on to a skin surface of a wearer;
collecting said biofluid from said skin surface via capillary action, a pressure differential or a combination of these; and
determining a property of said biofluid via said at least one colorimetric sensor.

46. The method of claim 45, wherein said step of collecting said biofluid is at least partially performed in the wet or aquatic environment.

47. The method of claim 45, wherein said step of determining said property of said biofluid is quantification of biofluid volume or amount, flow rate, composition or any combination thereof.

48. The method of claim 45, wherein said epidermal microfluidic system further comprises a temperature sensor and said method further comprises measuring a temperature of said skin surface.

49. An epidermal microfluidic system for use in a wet environment, the system comprising:
- a flexible substrate;
- a microfluidic inlet conduit network at least partially embedded in or supported by the flexible substrate;
- a biofluid inlet fluidically connected to the microfluidic inlet conduit network to provide a biofluid from a skin surface to the microfluidic inlet conduit during use;
- a microfluidic outlet conduit network fluidically connected to the microfluidic inlet conduit network and configured to relieve gas back pressure from the microfluidic inlet conduit network and sized to maintain liquid integrity of the system from the wet environment during use;
- at least one colorimetric sensor;
- a capping layer formed to cover a skin-facing surface of the flexible substrate and comprising a first auxiliary inlet aligned with the biofluid inlet, or formed to cover an outer-facing surface of the flexible substrate; and an adhesive layer comprising a second auxiliary inlet fluidically aligned with the biofluid inlet, wherein when the capping layer is formed to cover the outer-facing surface of the flexible substrate, the flexible substrate is positioned between the adhesive layer and the capping layer and the microfluidic inlet conduit network is embedded in the capping layer; and when the capping layer is formed to cover the skin-facing surface of the flexible substrate, the adhesive layer is positioned on at least a portion of an exposed surface of the capping layer; and wherein the microfluidic inlet conduit network comprises one or more passive valves or one or more active valves configured to allow for time dependent collection, analysis or storage of said biofluid.

50. The system of claim 49, wherein at least a portion of the passive or active valves is direction selective valves, selective super absorbent polymer (SAP) valves, hydrophobic valves, or a combination thereof.

51. The device of claim 49, wherein at least a portion of the passive or active valves is configured to close after a reservoir or channel is filled with said biofluid, thereby preventing loss or release of said biofluid from the filled reservoir or channel.

52. An epidermal microfluidic system for use in a wet environment, the system comprising:
a flexible substrate;
a microfluidic inlet conduit network at least partially embedded in or supported by the flexible substrate;
a biofluid inlet fluidically connected to the microfluidic inlet conduit network to provide a biofluid from a skin surface to the microfluidic inlet conduit during use;
a microfluidic outlet conduit network fluidically connected to the microfluidic inlet conduit network and configured to relieve gas back pressure from the microfluidic inlet conduit network and sized to maintain liquid integrity of the system from the wet environment during use, wherein the microfluidic outlet conduit network comprises a biofluid outlet having a characteristic dimension selected to prevent liquid backfilling from the wet environment; and
at least one colorimetric sensor.

53. An epidermal microfluidic system for use in a wet environment, the system comprising:
a flexible substrate;
a microfluidic inlet conduit network at least partially embedded in or supported by the flexible substrate;
a biofluid inlet fluidically connected to the microfluidic inlet conduit network to provide a biofluid from a skin surface to the microfluidic inlet conduit during use;
a microfluidic outlet conduit network fluidically connected to the microfluidic inlet conduit network and configured to relieve gas back pressure from the microfluidic inlet conduit network and sized to maintain liquid integrity of the system from the wet environment during use;
a plurality of reservoir chambers, each reservoir chamber fluidically connected with the microfluidic inlet conduit network; and
a plurality of colorimetric sensors positioned in fluidic communication with the microfluidic inlet network, wherein each of the of the plurality of colorimetric sensors comprise one or more color-responsive reagents for quantification of a biofluid volume or amount, flow rate, composition or any combination of thereof, and wherein the one or more color-responsive reagents are insensitive to humidity.

54. An epidermal microfluidic system for use in a wet environment, the system comprising:
a flexible substrate;
a microfluidic inlet conduit network at least partially embedded in or supported by the flexible substrate;
a biofluid inlet fluidically connected to the microfluidic inlet conduit network to provide a biofluid from a skin surface to the microfluidic inlet conduit during use;
a microfluidic outlet conduit network fluidically connected to the microfluidic inlet conduit network and configured to relieve gas back pressure from the microfluidic inlet conduit network and sized to maintain liquid integrity of the system from the wet environment during use;
at least one colorimetric sensor; and
a plurality of reservoir chambers, each reservoir chamber fluidically connected with the microfluidic inlet conduit network,
wherein the microfluidic outlet conduit network maintains the liquid integrity of the system with the surrounding environment by preventing introduction of liquid into the plurality of reservoir chambers.

* * * * *